United States Patent
Velghe et al.

(10) Patent No.: US 6,544,480 B1
(45) Date of Patent: Apr. 8, 2003

(54) DEVICE AND RELATED METHOD FOR DISPENSING SMALL VOLUMES OF LIQUID

(75) Inventors: Franck Velghe, Astene-Deinze (BE); Werner De Beukeleer, Boechout (BE); Chris Roelant, Leuven (BE); Rudi Pauwels, Bonheiden (BE)

(73) Assignee: Tibotec BVBA (BE)

( * ) Notice: Subject to any disclaimer, the term of this patent is extended or adjusted under 35 U.S.C. 154(b) by 0 days.

(21) Appl. No.: 09/426,708

(22) Filed: Oct. 26, 1999

(51) Int. Cl.$^7$ .......................... B01L 3/02; G01N 21/00; G01N 1/10; B32B 27/04
(52) U.S. Cl. ...................... 422/100; 422/64; 436/180; 73/863.32; 73/864.01; 73/864.11; 73/864.15; 73/864.17
(58) Field of Search ................. 422/100, 64; 436/180; 73/863.32, 864.01, 864.11, 864.15, 864.17

(56) References Cited

U.S. PATENT DOCUMENTS

| | | | |
|---|---|---|---|
| 3,650,306 A | * | 3/1972 | Lancaster |
| 4,029,470 A | * | 6/1977 | Wilkins et al. ............... 8/94.11 |
| 4,106,911 A | * | 8/1978 | Marcelli ....................... 23/259 |
| 4,158,035 A | * | 6/1979 | Haase et al. ................. 422/100 |
| 4,276,048 A | | 6/1981 | Leaback ....................... 23/230 |
| 4,459,265 A | * | 7/1984 | Berglund ..................... 422/64 |
| 4,593,728 A | * | 6/1986 | Whitehead et al. ........... 141/98 |
| 4,774,055 A | * | 9/1988 | Wakatake et al. ............. 422/64 |
| 5,147,610 A | * | 9/1992 | Watanabe et al. ............. 422/64 |
| 5,204,268 A | * | 4/1993 | Matsumoto ................... 436/44 |
| 5,226,462 A | * | 7/1993 | Carl |
| 5,425,918 A | * | 6/1995 | Healey et al. |
| 5,439,646 A | * | 8/1995 | Tanimizu et al. ............. 422/64 |
| 5,849,598 A | | 12/1998 | Wilson et al. ............... 436/180 |
| 5,882,930 A | | 3/1999 | Baier .......................... 436/49 |
| 6,027,691 A | * | 2/2000 | Watts et al. .................. 422/64 |
| 6,042,786 A | * | 3/2000 | Oonuma et al. .............. 422/64 |
| 6,132,582 A | * | 10/2000 | King et al. |
| 6,183,693 B1 | * | 2/2001 | Bogen et al. ................. 422/64 |
| 6,258,324 B1 | * | 7/2001 | Yiu ............................. 422/100 |

FOREIGN PATENT DOCUMENTS

| | | | |
|---|---|---|---|
| GB | 2 008 767 | 6/1979 | |
| WO | 97/15394 | 5/1997 | ............. B01L/3/00 |
| WO | 97/16569 | 5/1997 | |
| WO | 98/01533 | 1/1998 | |
| WO | 98/21571 | 5/1998 | |
| WO | 99/30154 | 6/1999 | |

OTHER PUBLICATIONS

PCT Application No. PCT/IB98/01399 filed Sep. 8, 1998 entitled "Method for the rapid screening of analytes".
Ekins et al., "Multiananlyte microspot immunoassay. The microanalytical 'compact disk' of the future," *Ann. Biol. Clin.*, (1992) 50, pp. 337–353.
Sigal et al., "Approaches and Technologies for Screening Large Combinatorial Libraries," *Combinatorial Chemistry and Molecular Diversity in Drug Discovery*, 1998, pp. 433–443.

* cited by examiner

Primary Examiner—Jill Warden
Assistant Examiner—Brian R. Gordon

(57) ABSTRACT

A device and related method for dispensing liquid. The device includes a housing configured to contain a plurality of liquid dispensing members containing a liquid and configured to contain a receiving member in a receiving position to receive the liquid from the plurality of liquid dispensing members. The housing defines a first pressure chamber and a second pressure chamber. The first pressure chamber is capable of being sealed relative to the second pressure chamber. The device also includes a differential pressure generator operably connected to one of the first and second pressure chambers. The generator is capable of generating a pressure differential between the first and second pressure chambers to cause the plurality of liquid dispensing members to dispense liquid onto the receiving member.

39 Claims, 24 Drawing Sheets

US 6,544,480 B1

DEVICE AND RELATED METHOD FOR DISPENSING SMALL VOLUMES OF LIQUID

BACKGROUND OF THE INVENTION

1. Field of the Invention

The present invention relates to a device and related method for dispensing small volumes of liquid, and more specifically to such a device and method for simultaneously dispensing liquid from a plurality of liquid dispensing members into a receiving plate.

2. Discussion of the Related Art

Currently, screening programs identify potential compounds for use as drugs. Specifically, drug discovery often depends on high throughput screening (HTS) techniques to screen compounds, such as liquid analytes, as potential drug candidates. In HTS, an increasingly high number of compounds, most often organized in libraries, are tested simultaneously. Simultaneous testing of a high number of compounds is due, at least in part, to technological developments, such as automated testing, combinatorial chemistry, and the polymerase chain reaction. An increased demand for new and better drugs for a variety of diseases also drives the simultaneous testing of a high number of compounds.

The standard library, or plate, for use in HTS has a 96 well per plate format. Thus, HTS systems typically have been developed for use with this format. For increasing throughput requirements and simultaneous testing of more compounds, HTS has been using higher density plates with, for example, 384, 864, 1536, and 9600 wells. These increased density plates present new problems. Particularly, the transfer of compounds into the plate often limits the testing process, as the compounds have to be brought into a high density often at a different geometry. Subsequent dispensing of solutions onto these high density plates during the testing process also poses difficulties. In addition, the introduction of robots and other forms of automation in drug discovery has led to new concerns, such as, for example, concerns regarding the speed, parallelization, volume, and reliability of robotic systems.

Current transfer and dispensing systems often rely on glass pipettors with plungers (such as the Hydrasystem™ of Robin Scientific Inc.), needles or pins, or piezo-electric pipettors. Each such system has drawbacks. For example, current pipetting systems include the relatively high cost of pipet tips, which can be substantial in automated testing. The use of needles and pins for liquid dispensing, although less expensive, lacks control over the dispensed volume and does not provide for multiple replicas to be made. Current piezoelectric pipettors usually provide increased control over dispensed volume but typically are relatively large, difficult to miniaturize, and not suitable for massive parallel dispensing due to their relative expense. Current glass pipettors, although not as expensive, share many of the disadvantages of current piezo electric pipettors and may not dispense liquid in volumes as small as 100 nanoliters.

SUMMARY OF THE INVENTION

To overcome the drawbacks of conventional systems and in accordance with the purpose of the invention, the invention comprises a device for dispensing liquid. The device includes a housing configured to contain a plurality of liquid dispensing members containing a liquid and configured to contain a receiving member in a receiving position to receive the liquid from the plurality of liquid dispensing members. The housing defines a first pressure chamber and a second pressure chamber. The first pressure chamber is capable of being sealed relative to the second pressure chamber. The device also includes a differential pressure generator operably connected to at least one of the first and second pressure chambers. The generator is capable of generating a pressure differential between the first and second pressure chambers to cause the plurality of liquid dispensing members to dispense liquid into the receiving member.

According to an embodiment of the inventive device, the first pressure chamber is in fluid communication with ambient environment. According to another embodiment, the device includes a plug to selectively seal the second pressure chamber from the ambient environment. The plug may include a valve in fluid communication with the second pressure chamber.

According to a further embodiment of the device, the housing is configured to hold a first end of each of the plurality of liquid dispensing members in the first pressure chamber and a second end of each of the plurality of liquid dispensing members and the receiving member in the second pressure chamber.

In an even further embodiment of the device, the differential pressure generator is in communication with the second pressure chamber and is capable of creating a pressure in the second pressure chamber that is lower than a pressure in the first pressure chamber.

In another embodiment of the inventive device, the differential pressure generator is in communication with the second pressure chamber and includes a movable member capable of altering a volume of the second pressure chamber to alter a pressure within the second pressure chamber. In an embodiment, the movable member seals the second pressure chamber from ambient environment. The movable member may include a flexible member between a pair of movable plates.

In another embodiment, the device of the present invention includes a support adjacent to the housing and capable of supporting a plurality of receiving members. The support may be movable relative to the housing to position a receiving member in the housing. In an embodiment, the support is moveable relative to the housing to sequentially position receiving members in the housing one receiving member at a time.

In a further embodiment of the device, the second pressure chamber is configured to contain the receiving member and the device includes a positioning device within the second pressure chamber capable of positioning the receiving member in the receiving position. The positioning device may include a movable element having an end capable of gripping the receiving member.

According to another aspect, the invention comprises a device for dispensing liquid that includes a holder having a plurality of liquid dispensing members mounted therein. Each of the plurality of liquid dispensing members is configured to contain a liquid between first and second ends of the dispensing member. In an embodiment, each of the members is configured to contain a different liquid between the first and second ends. A receiving member is capable of receiving liquid dispensed from the plurality of liquid dispensing members. A housing defines a first pressure chamber and a second pressure chamber. The first pressure chamber is capable of being sealed relative to the second pressure chamber. A differential pressure generator is operably connected to at least one of the first and second pressure chambers. The generator is capable of generating a pressure differential between the first and second pressure chambers. The housing is configured to contain the holder in a dispensing position and the receiving member in a receiving position so that the generation of the pressure differential causes the plurality of liquid dispensing members to dispense liquid onto the receiving member.

In an embodiment of the inventive device, the holder seals the first pressure chamber from the second pressure chamber.

In another embodiment, the first pressure chamber is in fluid communication with ambient environment and the second pressure chamber is capable of being selectively sealed from the ambient environment.

In a further embodiment, each of the plurality of liquid dispensing members is a capillary. In an even further embodiment of the inventive device, the housing is configured to contain the holder so that the first end of each capillary is in the first pressure chamber and the second end of each capillary is in the second pressure chamber.

In yet another embodiment of the inventive device, the differential pressure generator is in communication with the second pressure chamber and capable of creating a pressure in the second pressure chamber that is lower than a pressure in the first pressure chamber. According to an embodiment, the differential pressure generator includes a movable member capable of altering a volume of the second pressure chamber to create the pressure within the second pressure chamber. The movable member may seal the second pressure chamber from ambient environment. The movable member also may include a flexible member. According to an embodiment, the flexible member is between a pair of movable plates.

Another embodiment of the inventive device further includes a support adjacent to the housing and capable of supporting a plurality of receiving members. In another embodiment, the support is movable relative to the housing to sequentially position receiving members in the housing one receiving member at a time.

According to a further embodiment of the inventive device, the second pressure chamber is configured to contain the receiving member, and the device further includes a positioning device within the second pressure chamber capable of positioning the receiving member in the receiving position. In an embodiment, the positioning device includes a movable element having an end capable of gripping the receiving member.

According to a further aspect, the invention comprises a method of dispensing liquid from a plurality of liquid dispensing members onto a receiving plate. The method includes the steps of positioning a plurality of liquid dispensing members into a dispensing device so that a first end of each dispensing member is contained in a first pressure chamber of the dispensing device and a second end of each dispensing member is contained in a second pressure chamber of the dispensing device; positioning a receiving plate in the second chamber relative to the second ends of the dispensing members; and creating a pressure differential between the first and second pressure chambers so that the dispensing members dispense liquid into the receiving plate.

According to an embodiment of the method, the creating step includes lowering a pressure in the second pressure chamber. In an embodiment, lowering the pressure in the second pressure chamber includes increasing a volume of the second pressure chamber. The volume may be increased by moving a movable member.

According to another embodiment, the inventive method further includes sealing the first pressure chamber from the second pressure chamber. The sealing step may include positioning a holder of the plurality of liquid dispensing members between the first pressure chamber and the second pressure chamber.

In another embodiment of the inventive method, the first pressure chamber is exposed to an environment, and the method further includes sealing the second pressure chamber from the environment prior to the creating step.

In yet another embodiment, the method further includes, subsequent to the pressure differential creating step, the step of equalizing pressures within the first and second pressure chambers.

An embodiment of the method further includes the steps of removing the receiving plate from the second chamber, and repeating the receiving plate positioning step, the pressure differential creating step, and the pressure equalizing step to dispense liquid onto a subsequent receiving plate.

In a further embodiment of the method each of the plurality of dispensing members is a capillary, the first end is an open top end, and the second end is an open bottom end.

It is to be understood that the foregoing general description and the following detailed description are exemplary and explanatory only and are not restrictive of the invention as claimed.

BRIEF DESCRIPTION OF THE DRAWINGS

The accompanying drawings are included to provide a further understanding of the invention and are incorporated in and constitute part of the specification, illustrate preferred embodiments of the invention, and, together with a description, serve to explain the principles of the invention.

DETAILED DESCRIPTION OF THE PREFERRED EMBODIMENTS

Figure 1:
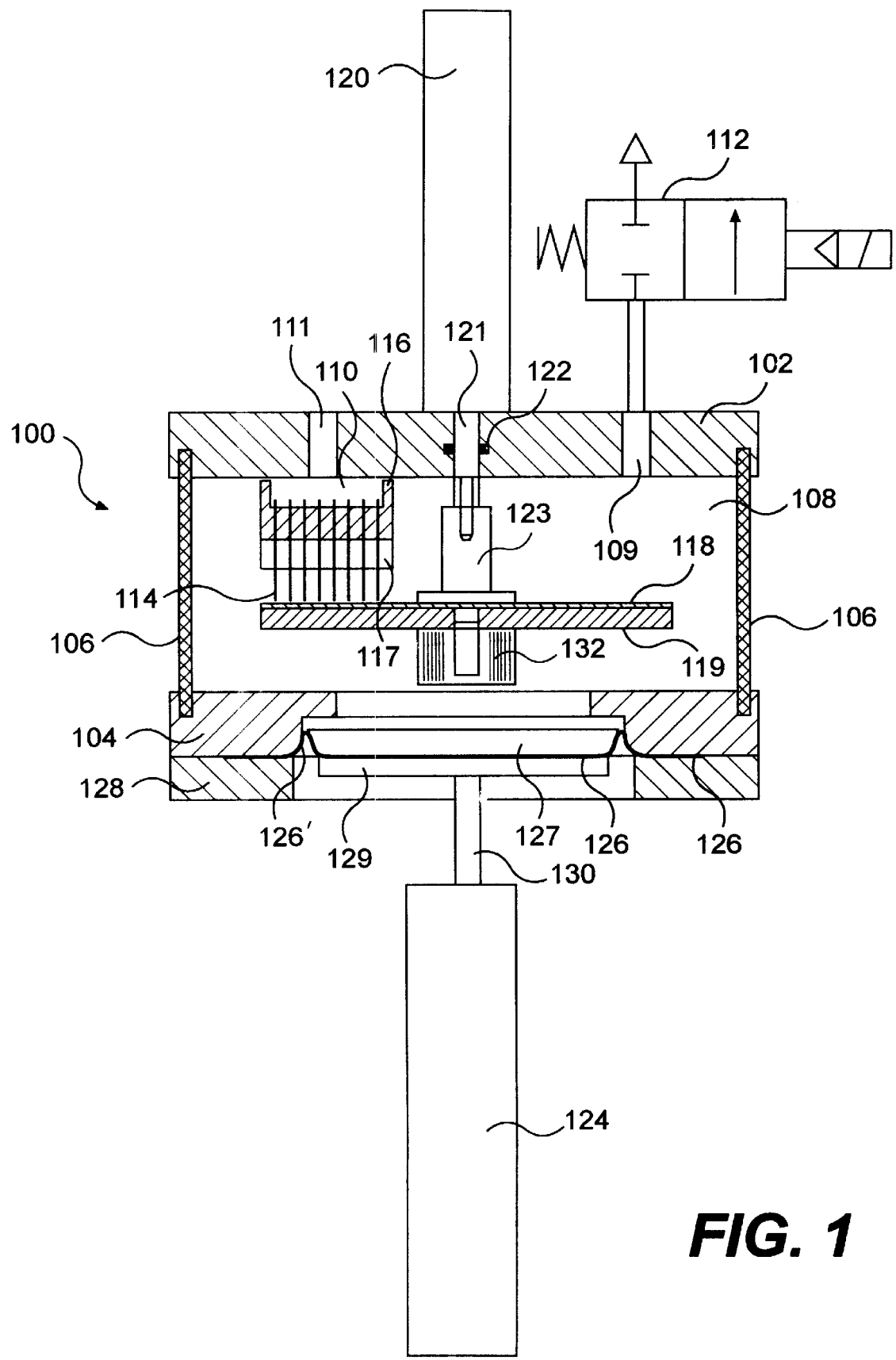
FIG. 1 is a cross-sectional view of a dispensing device according to an embodiment of the present invention.

The present invention relates to a device and related method for simultaneous dispensing of liquid from a plurality of liquid dispensing members into a receiving plate. The device and related method apply to liquid dispensing of very small volumes at high densities, i.e. number of dispensings per area, in parallel. The device and method are particularly suitable for use in automated drug screening or combinatorial chemistry. However, the principles of the device and the related method may be used in other applications requiring controlled dispensing of very small amounts of liquid in any specific format, or arrangement. The invention also relates to dispensing any liquid, including liquid with or without cells and viscous solutions such as gels in liquid state.

Another advantage of the inventive device and related method includes miniaturization of parts, including the liquid dispensing members, so that disposable capillaries may be used. The smaller parts, and specifically capillaries, results in the ability to dispense very small volumes of liquid, reducing the costs from use of rare or expensive chemicals or analytes. The dispensed volume can range from one microliter to as low as ten nanoliters.

The device and related method also have flexibility in the density of the dispensed volumes and in the type and size of the specific geometries of dispensing. For example, the device may dispense liquid or print liquid spots at densities ranging from the present standard of 1–4 per cm2 up to 100 per cm2 or higher in any geometric pattern, such as round, square, or an irregular shape. The device and method also may be used to print multiple identical prints from a it single set of capillaries, or other liquid dispensing members, so that numerous tests may be performed on the same analytes. A further advantage of the device and method of the present invention includes the massive dispensement of liquid in parallel. For example, in automatic drug screening, the device may dispense liquid onto receiving plates with much higher than the conventional 96 wells per plate. Instead, dispensing can occur onto plates having hundreds or thousands of wells with the same footprint dimensions. As a further example, in combinatorial chemistry, standard parallel synthesis typically occurs in a maximum of 48 vials at a time with liquid transferred from one needle. The inventive device and method may be used for parallel liquid dispensing to support simultaneous synthesis in a much higher number of wells.

In addition, the inventive device and related method may be fully automated, and is preferably computer controlled. This increases the speed of dispensing liquid into multiple receiving plates and minimizes human operation and error.

The device and its related method operate under rapid, controlled relative changes in pressure above and below the liquid dispensing members. More specifically, a dispensing member such as a glass capillary holds a column of liquid by surface tension forces between open top and bottom ends. A rapid, controlled relative pressure drop at the bottom end will force liquid to be dispensed from the bottom of the capillary. Depending on various possible factors, including the type of capillary (its size, shape, and configuration), the viscosity of the liquid therein, and the relative pressure change, a drop of liquid may be released from the capillary or a drop may be suspended from the bottom end. If the former, the drop may be received by a receiving plate that may include wells corresponding to the number and arrangement of capillaries. If the latter, a receiving plate with or without wells may be accurately positioned relative to the bottom end of the capillaries to receive a printed spot of liquid from each capillary in a predetermined arrangement. The optimal gap between the receiving plate and the end of the capillary will depend on, among other things, the width of the capillary, the volume of liquid in the capillary, the pressure differential generated across the capillary, the properties of the liquid in the capillary, for example the viscosity of the liquid, and the properties of the receiving plate, for example the adhesive characteristic of the plate material. Through appropriate experimentation, one skilled in the art may determine the optimal size of the gap according to these and other various factors to result in the desired liquid print.

The accompanying Figures and the following description refer to the present preferred and exemplary embodiments of the inventive device and related method. Like reference numerals refer to like parts in the various Figures.

FIG. 1 shows a dispensing device 100 according to an embodiment of the present invention. Device 100 includes a housing having a top 102, a bottom 104, and sides 106 that define a pressure chamber 108. A support 116 extends from the bottom surface of housing top 102. Support 116 supports a holder 117 that contains a plurality of liquid dispensing members, for example, capillaries 114. The plurality of capillaries may be a grid of, for example, eight rows of twelve capillaries per row. Each capillary 114 contains a liquid solution to be dispensed. Capillaries 114 are affixed to holder 117 preferably by an ultraviolet-cured glue on the outside of each capillary 114 or by an other suitable adhesive or fixing means. The liquid dispensing members may take forms other than capillaries for dispensing small volumes of liquid, for example micropipettes.

Housing top 102 and support 116 with holder 117 therein define another pressure chamber 110 hermetically sealed from pressure chamber 108. Chamber 110 is in fluid communication with ambient surroundings through opening 111. A valve 112 couples to housing top 102 and is in fluid communication with chamber 108 via port 109. Valve 112 is preferably a fast-responding, pneumatically operable valve. However the scope of this invention includes other suitable types of valves for altering the pressure within chamber 108 in a manner described below.

A receiving plate 118 mounts onto a mounting plate 119 within chamber 108. Receiving plate 118 is positioned at a right angle relative to capillaries 114 for receiving the liquid solution in each capillary 114. Receiving plate 118 may be separated from the bottom ends of capillaries 114 by an optimal distance, as discussed above. A bolt 132 or other like fastening mechanism may be used to fix receiving plate 118 to mounting plate 119. Alternatively, receiving plate 118 may sit loosely in position on mounting plate 119. Mounting plate 119 connects to an end of a linear servodrive 120 through a rod 121 and shaft 123. A seal 122, such as an O-ring, seals around rod 121 to seal chamber 108 from ambient conditions. Servodrive 120 rotatably and vertically positions receiving plate 118 relative to capillaries 114. Various types of suitable actuators may be used to accurately position receiving plate 118 relative to capillaries 114 and still be within the scope of this invention.

Housing bottom 104 couples to a bottom plate 128. Housing bottom 104 and bottom plate 128 each include a central throughhole. Top and bottom round plates elements 127 and 129 float within the central throughholes of bottom 104 and plate 128 by provision of a thin, circular flexible membrane 126. Round plate elements 127, 129 and membrane 126 act as a differential pressure generator, as will be described. Flexible membrane 126 is firmly positioned between housing bottom 104 and bottom plate 128 and extends into the throughholes of bottom 104 and plate 128 to be firmly sandwiched between top and bottom round plate elements 127 and 129. The portion of membrane 126 within the throughholes and not sandwiched between elements 127, 129 separates chamber 108 from ambient environment. This membrane portion, identified by reference numeral 126', also has some gather (i.e. fold or wrinkle), as shown in FIG. 1, that permits floating plate elements 127, 129 to move vertically. That vertical movement alters the volume of chamber 108 and creates a pressure differential between chambers 108 and 110, as will be described. A linear servodrive 124 couples to bottom round plate element 129 via a shaft 130 to control vertical displacement of plates 127, 129 and flexible membrane 126. Once again, other types of suitable actuators may be used to accurately displace these elements vertically and still be within the scope of this invention.

In operation, housing top 102 may be lifted or otherwise separated from housing sides 106 to position receiving plate 118 onto mounting plate 119 and to position holder 117 with capillaries 114 onto support 116. Housing top 102 then may rejoin sides 106. Servodrive 120 then rotatably and vertically positions receiving plate 118 under capillaries 114. An open top of each capillary 114 is exposed to chamber 110, whereas as open bottom of each capillary 114 is exposed to chamber 108. At this point, because of equal pressures within chambers 108 and 110, equal pressures exist at the ends of capillaries 114 and a column of liquid, for example a buffer solution, is held within each capillary 114 by surface tension forces. This state is shown in capillary 114 at the right in FIG. 2.

Figure 2:
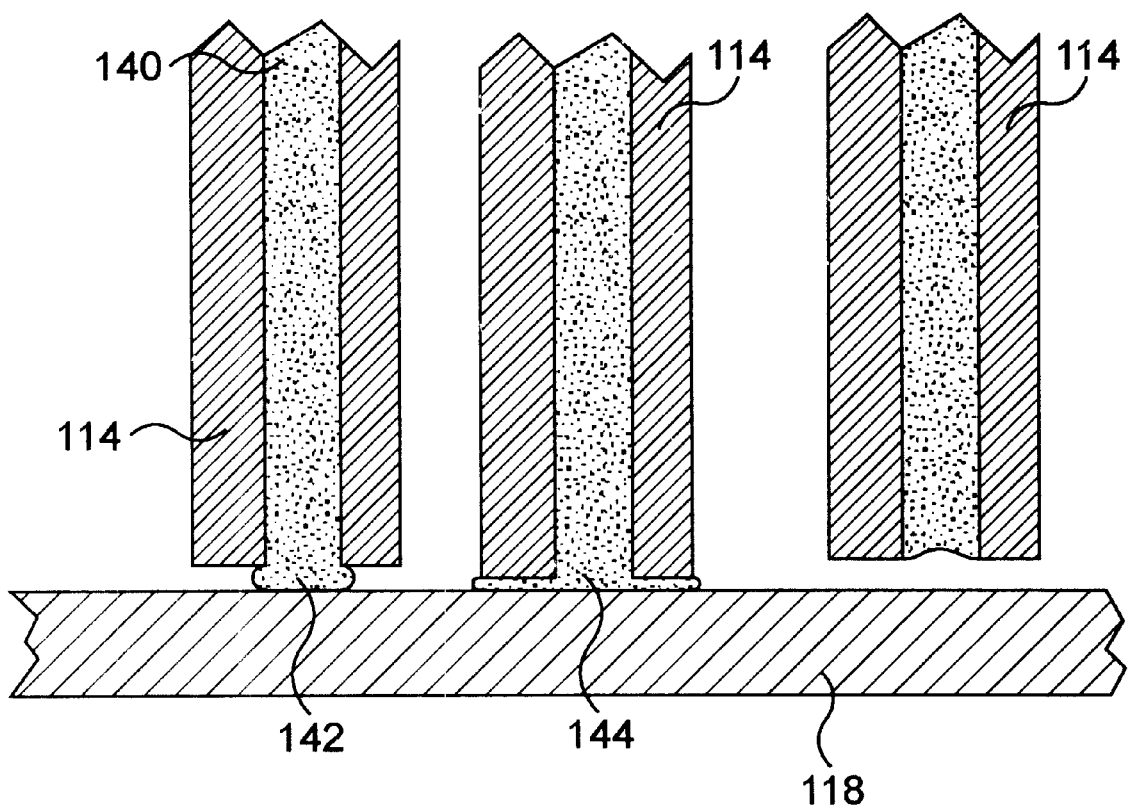
FIG. 2 is a cross-sectional view of capillaries dispensing liquid onto a receiving plate in a dispensing device according to an embodiment of the present invention.

A print cycle then begins by actuating servodrive 124 to move plates 127 and 129 vertically upwards. Chamber 108 then is plugged at port 109 via valve 112. While chamber 110 remains at ambient pressure due to opening 111, a pressure drop is created in chamber 108 by servodrive 124 displacing plates 127, 129 vertically downwards. That vertical displacement downwards increases the volume of chamber 108 to create the pressure drop. The pressure drop is preferably sudden and brief and performed in a controlled manner, as explained below, for example, in connection with FIG. 3. Thus, a lower pressure will exist in chamber 108 relative to chamber 110. A top of each capillary 114 therefore will be exposed to a greater pressure than a bottom of each capillary 114 and a difference in pressure results across the liquid in each capillary 114. This difference in pressure causes a microdroplet of liquid 142 to form at the bottom tip of each capillary 114, as shown in FIG. 2. Droplet 142 touches receiving plate 118 and accurate vertical positioning of receiving plate 118 relative to capillaries 114 forms an oblate (flattened) liquid spheroid 144 between the capillary tip and receiving plate 118, as also shown in FIG. 2. Liquid spheroid 144 leaves a printed spot on receiving plate 118. As explained above, depending on various factors, the capillary instead may release a drop of liquid.

After the brief, sudden pressure drop (which creates the printed spots), valve 112 is actuated to increase the pressure within chamber 108 and equalize the pressures within chambers 108 and 110. Valve 112 may perform these functions by opening port 109 and exposing chamber 108 to ambient surroundings. Servodrive 124 also may return plates 127, 129 and flexible member 126 to their original positions. At this point, capillary forces (surface tension) will dominate once again and microdroplet 142 will return into capillary 114. If desired, receiving plate 118 may be rotatably repositioned relative to capillaries 114 to print another copy of liquid solution onto receiving plate 118 from the same set of capillaries 114. When the desired number of print copies has been made onto plate 118, plate 118 may be removed from dispensing device 100 for use in chemical testing. Holder 117 and its capillaries 114 may be removed after printing the desired number of print copies and/or all the liquid within capillaries 114 is used.

Figure 3:
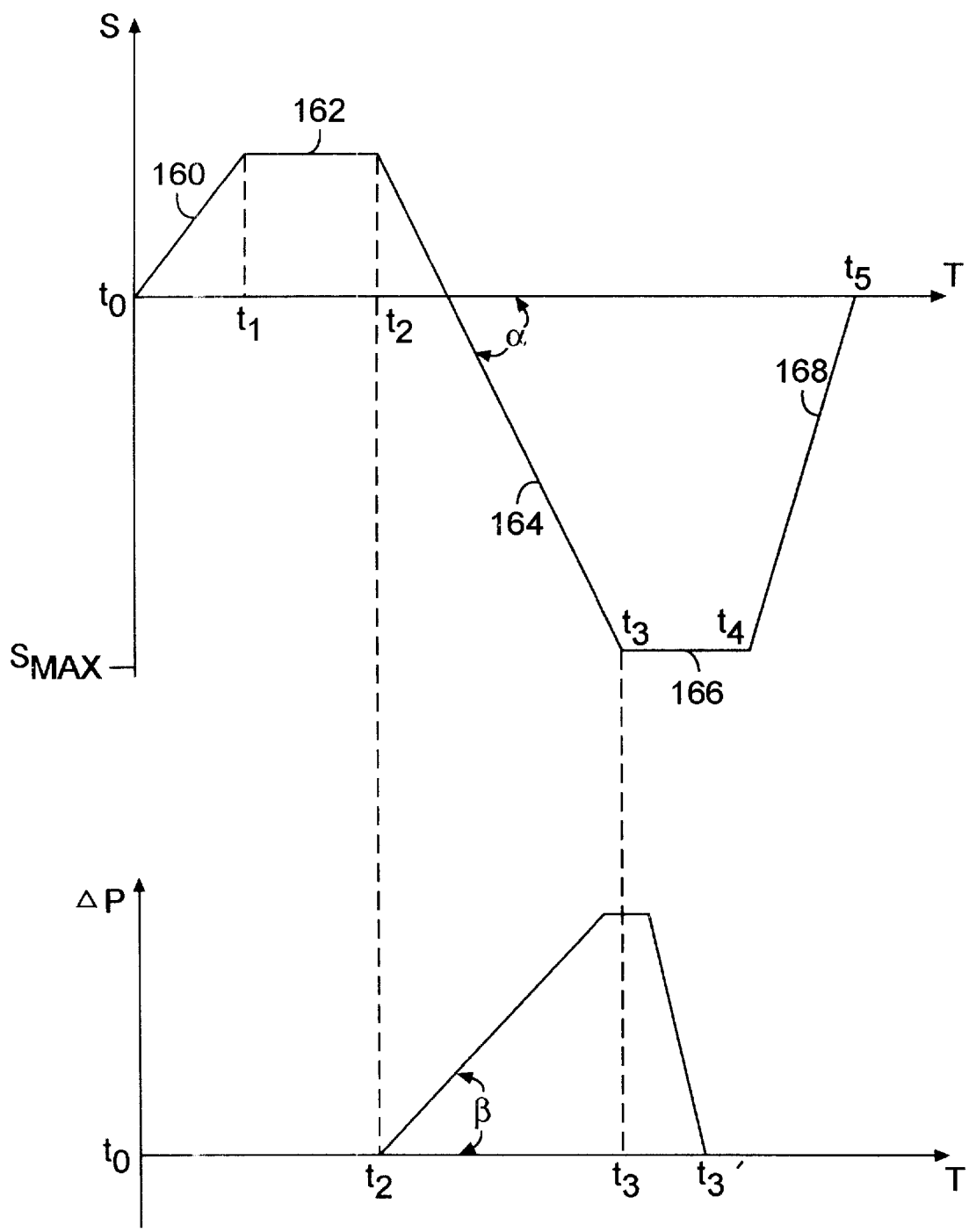
FIG. 3 is a graph of displacement of plate elements within the dispensing device of FIG. 1 and a graph of pressure differential in chambers of the dispensing device of FIG. 1.

The top graph in FIG. 3 shows an exemplary position curve as a function of time for plates 127, 129 and membrane 126. The bottom graph in FIG. 3 shows the absolute difference in pressure $\Delta P$ in chambers 108 and 110 as a function of time. Reference numeral 160 of the top graph (displacement v. time) represents the initial upwards displacement of plates 127, 129 and membrane 126 at the beginning of the print cycle. This upwards displacements occurs at approximately constant velocity until a time $t_1$. Between times $t_1$ and $t_2$, represented by reference numeral 162, plates 127, 129 and membrane 126 stay in position as chamber 108 is closed to ambient surroundings. Up until time $t_2$, the pressures within chambers 108 and 110 are equal, i.e. $\Delta P=0$.

From times $t_2$ to $t_3$ (reference numeral 164), plates 127, 129 and membrane 126 are moved downwards to create a pressure drop in chamber 108. The downwards displacement occurs at approximately constant velocity (angle represents the displacement velocity) and the absolute difference in pressure between chambers 108 and 110 is shown in the bottom graph of FIG. 3 (angle $\beta$ represents the pressure drop speed). Printing occurs during this time. The optimal displacement velocity and pressure drop speed are functions of, for example, the properties of the liquid to be dispensed and the capillary containing the liquid. An exemplary pressure drop may be in the range of approximately 20 to 30 mm $H_2O$ in a fraction of a second.

At time $t_3$, valve 112 is actuated to increase pressure within chamber 108. Pressure is increased until time $t_3'$ when the pressures within chambers 108 and 110 once again are equalized. Also beginning at time $t_3$, plates 127, 129 and membrane 126 initially stay in position (from times $t_3$ to $t_4$; reference numeral 166), and then return to their initial position (from times $t_4$ to $t_5$; reference numeral 168). The return to initial position occurs at approximately constant velocity and completes the print cycle.

FIG. 3 shows exemplary position and differential pressure curves. The present invention encompasses curves varying from those shown in FIG. 3. For example, during the stages represented by numerals 160, 164, and 168, velocity of the components can vary. Also, the relative times and displacements shown may be modified according to the preferred characteristics of the print cycle. It is also to be understood that a complete print cycle occurs rapidly, and preferably within seconds, and more preferably within a range of ten seconds or less. As a further modification from the curves shown in FIG. 3, increases in differential pressure may be achieved over time in a stepwise fashion for multiple dispensing. In such a case, at time intervals, the differential pressure may be increased rapidly in equal or unequal amounts so that dispensement occurs at each time interval.

FIGS. 4–9 and FIGS. 18–43 illustrate another preferred embodiment of a dispensing device 200 according to the present invention. FIGS. 10–17 illustrate a preferred embodiment of a holder and capillaries for use in device 200. Dispensing device 200 and the holder and capillaries for its use operate under very similar principles as dispensing device 100 described above. Much more detail of device 200 and its holder, however, are provided.

For purposes of describing its many components, dispensing device 200 can be thought of as having a turntable 310 in which one or more receiving plates 318 rest, a top portion above turntable 310, and a bottom portion below turntable 310. The top portion includes a print head 201. As shown in FIGS. 4–8, the main components of the top portion, including print head 201, include: an upper housing 202; upper and lower round plates 204 and 206 respectively; a flexible member 208; a mounting plate 218; upper, middle, and lower plates 220, 222, and 224 respectively; a linear servopositioner 214; a linear ball bush guide 226; a mounting block 228; and an air cylinder 230. Of these components, round plates 204 and 206, flexible member 208, and plates 218, 220, 222, and 224, comprise print head 201. All of these components and their relationship and connection to each other will now be described in detail.

Figure 18:
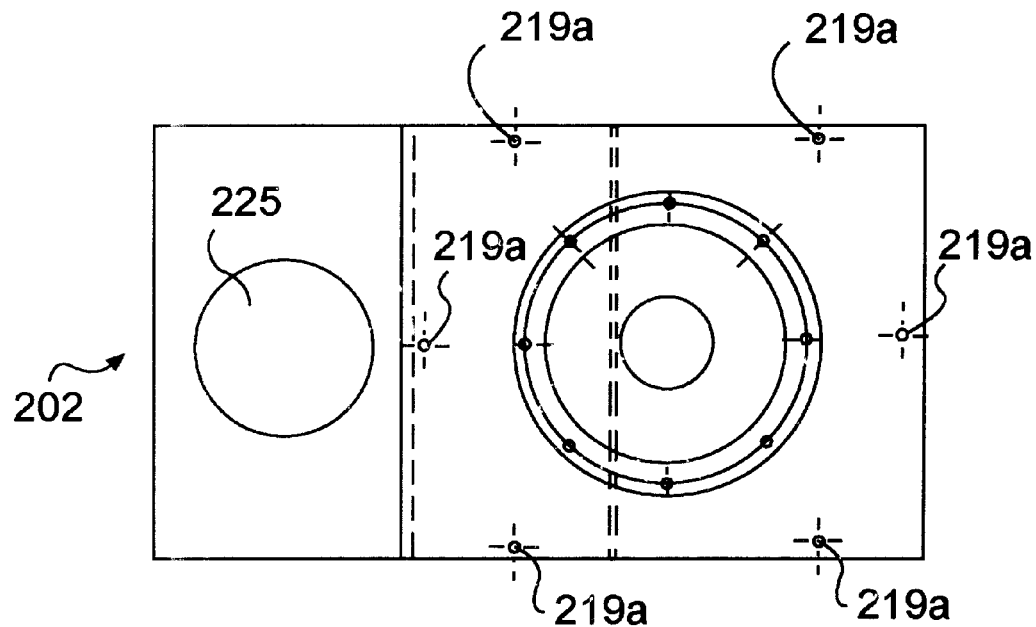
FIGS. 18–21 respectively are bottom, side, cross-sectional front, and top views of an upper housing of the device of FIG. 4, with FIG. 20 taken at line A—A in FIG. 21.
Figure 19:
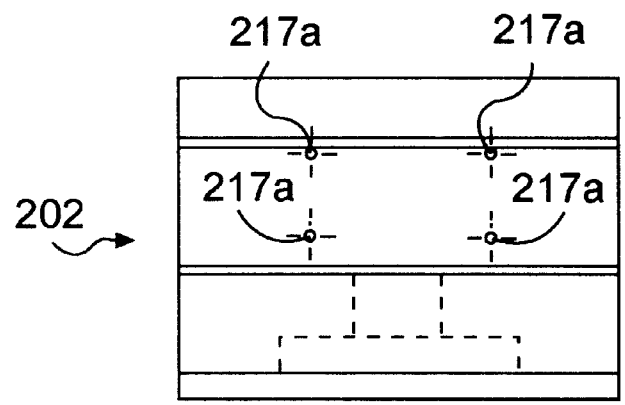
Figure 20:
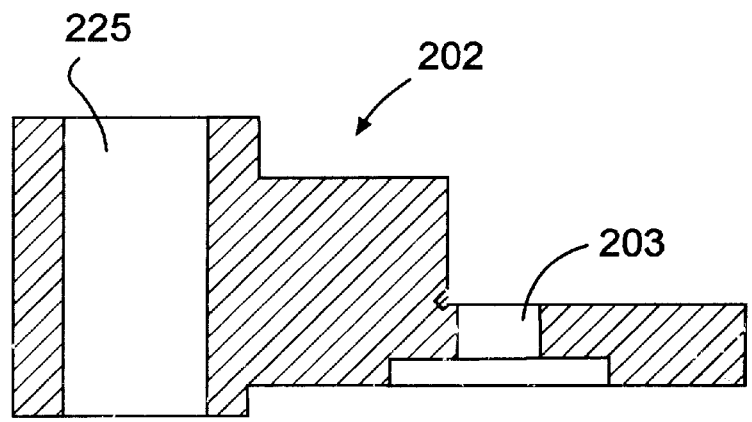
Figure 21:
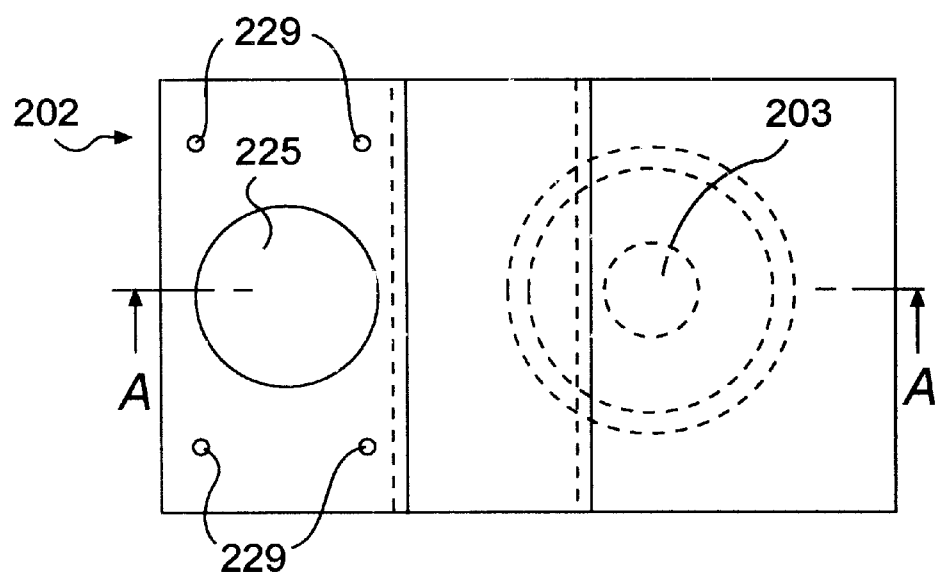

Upper housing 202 is shown in detail in FIGS. 18–21. FIG. 18 is a bottom view of housing 202, whereas FIGS. 19–21 are side, cross-sectional front, and top views respectively. Upper housing 202 includes a hole 203 to receive a shaft 215 of linear servopositioner 214. Servopositioner 214 mounts to upper housing 202 at points 217a via screws, bolts, or other like suitable connection means. The bottom portion of hole 203 receives upper and lower round plate elements 204, 206 between which a portion of flexible member 208 is sandwiched. Shaft 215 connects to upper round plate element 204. Upper housing 202 also includes a hole 225 to receive linear ball bush guide 226 to which housing 202 fixedly mounts. Mounting block 228 mounts to a top of upper housing 202 at mounting points 229 via pins, bolts, or other suitable fastening means.

Figure 43:
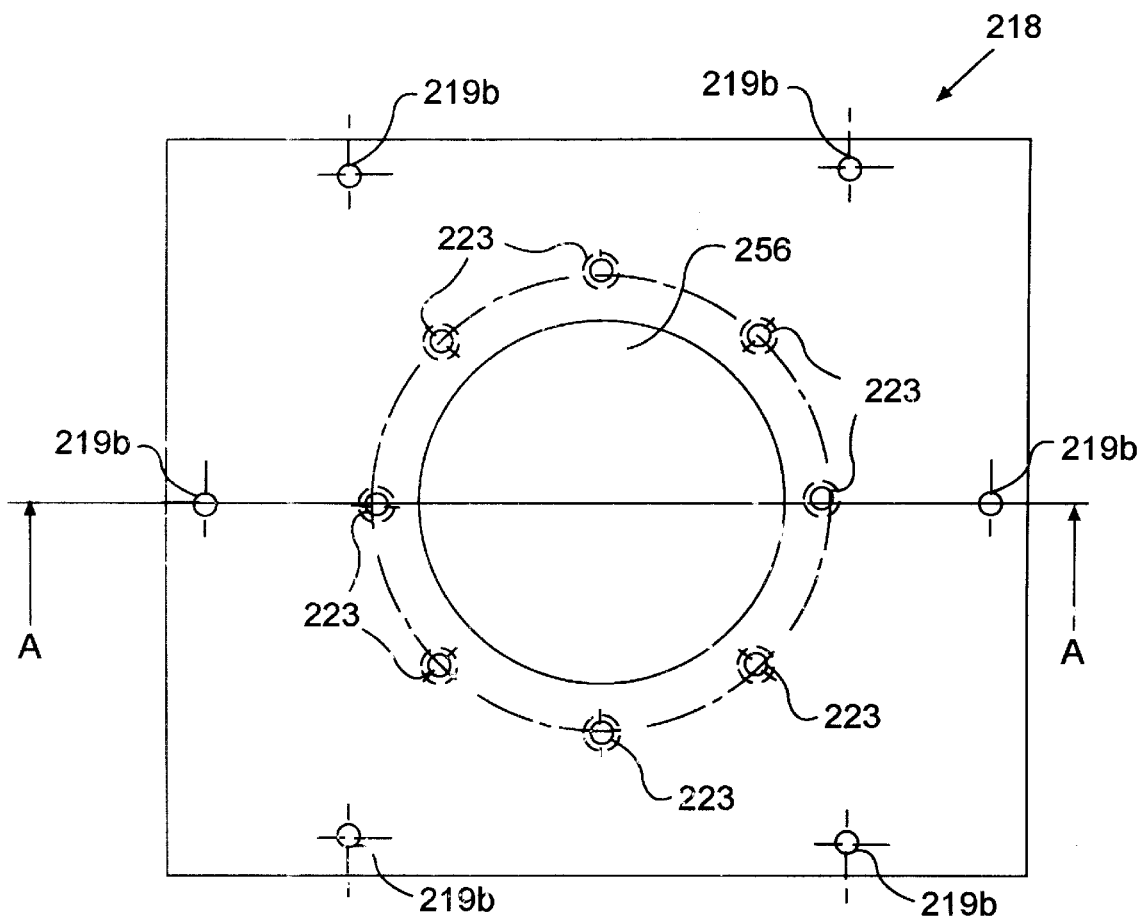
FIGS. 43–44 respectively are cross-sectional front and top views of a mounting plate of the print head of the device of FIG. 4, with FIG. 44 taken at line A—A of FIG. 43.
Figure 44:
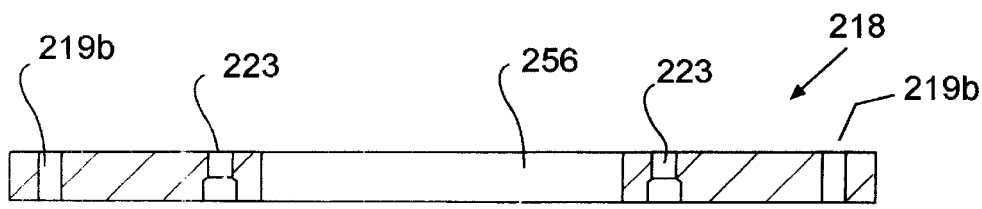

Mounting plate 218, shown in detail in FIGS. 43 and 44, is fixed to upper housing 202 at mounting points 219a (see FIG. 18) and mounting points 219b (see FIG. 43). Another portion of flexible member 208 is sandwiched between upper housing 202 and mounting plate 218. Mounting plate 218 includes a central hole 256 to receive upper and lower round plate elements 204, 206. A plurality of fixing points 223 (see FIG. 43) surround hole 256 and receive bolts or other suitable fastening means to secure flexible membrane 208 between housing 202 and mounting plate 218.

Figure 23:
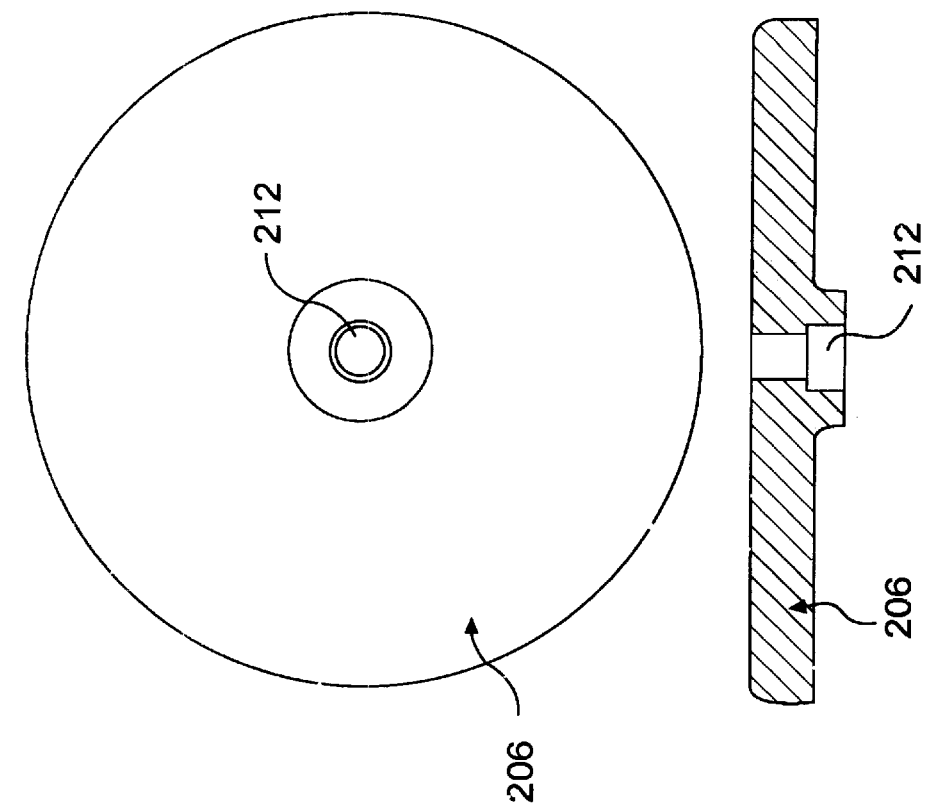
FIG. 23 is a bottom view and a cross-sectional side view of a lower round plate element of the device of FIG. 4.
Figure 22:
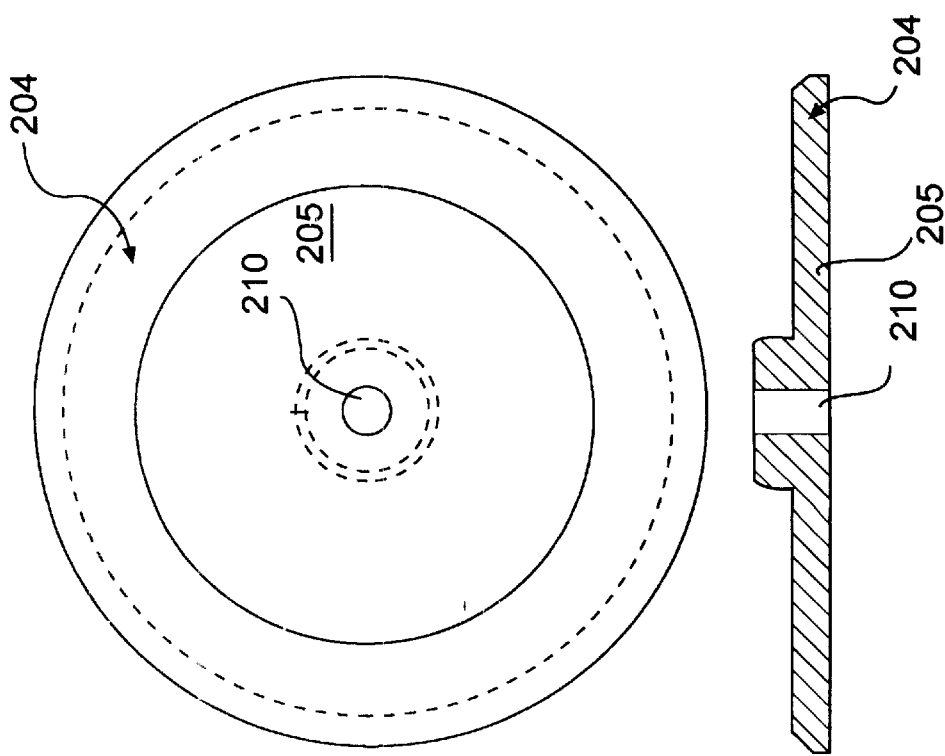
FIG. 22 is a bottom view and a cross-sectional side view of an upper round plate element of the print head of the device of FIG. 4.
Figure 24:
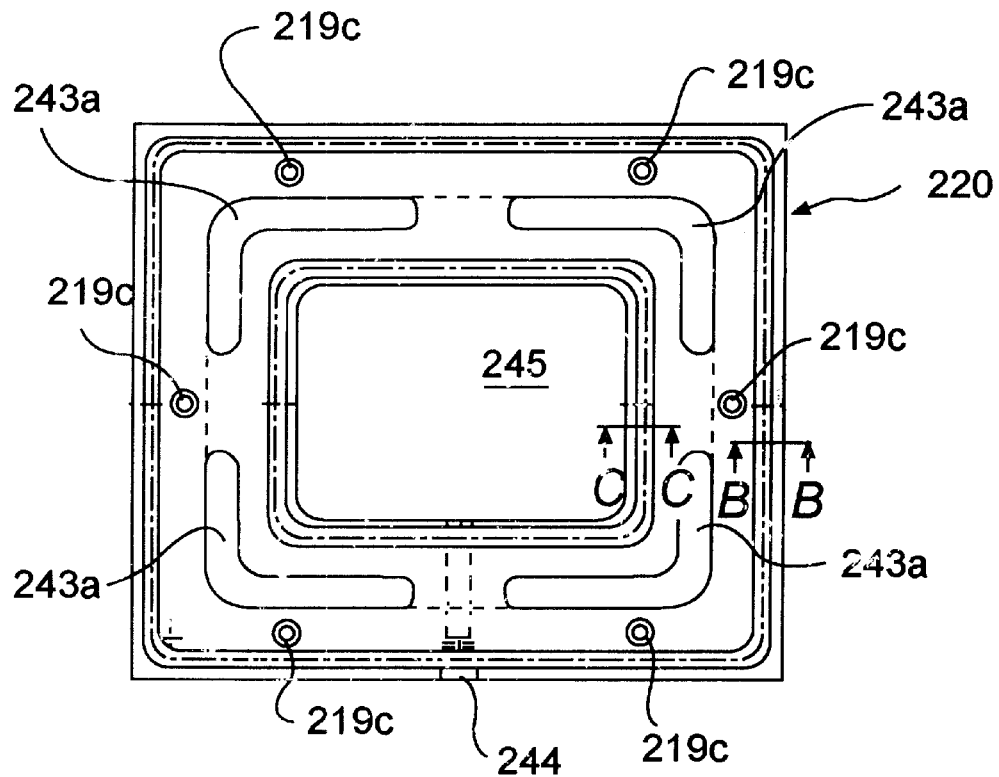
FIGS. 24–26 respectively are bottom, cross-sectional front, and top views of an upper plate of the print head of the device of FIG. 4, with FIG. 25 being taken at line A—A of FIG. 26.
Figure 25:
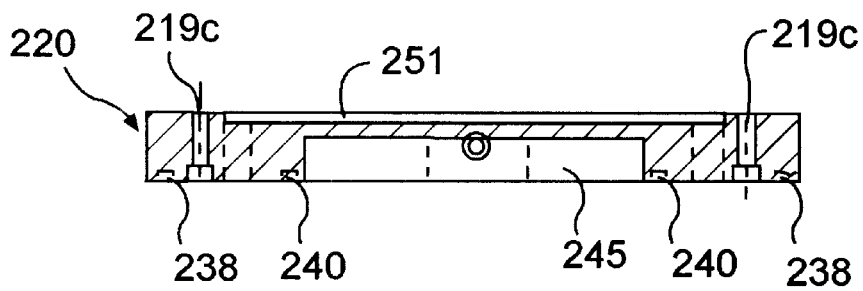
Figure 26:
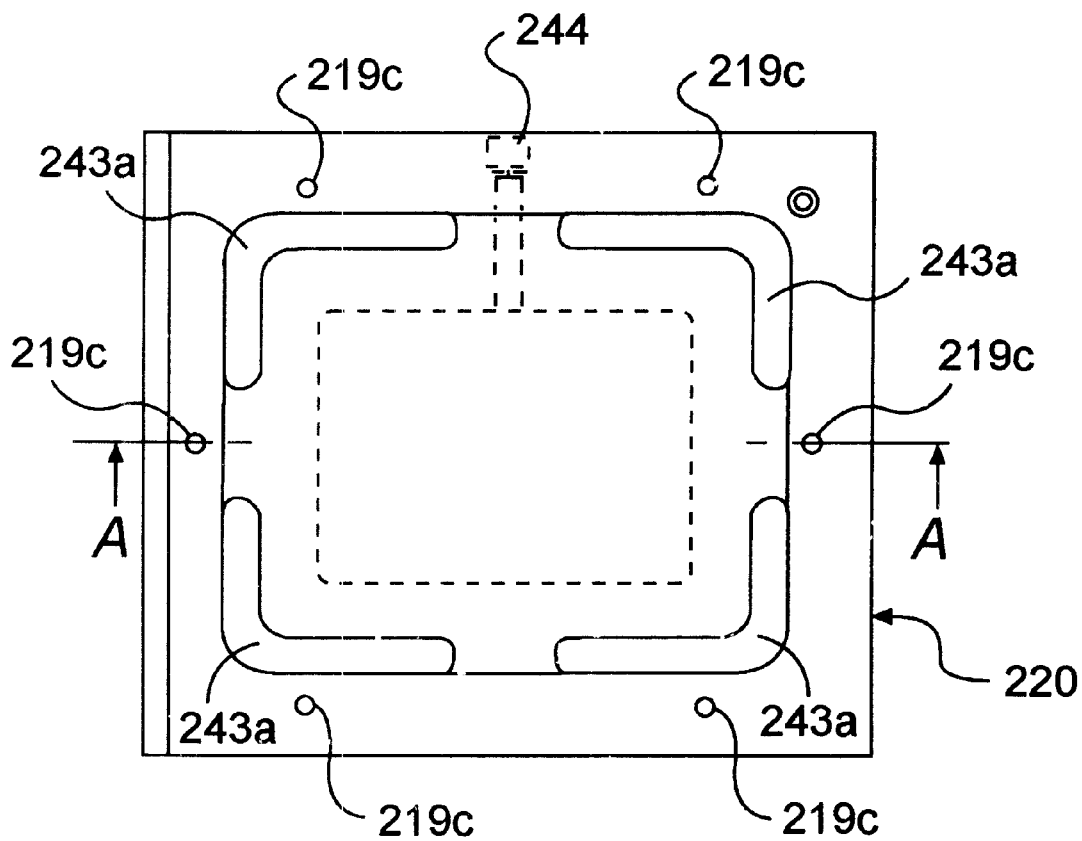
Figure 27:
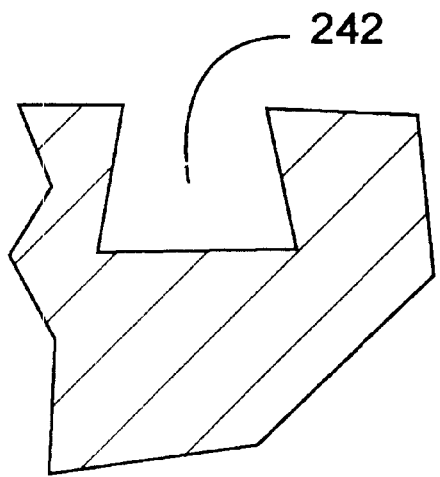
FIG. 27 is a partial cross-sectional view of the upper plate of FIGS. 24–26, showing a groove for an O-ring, taken at either line B—B or line C—C of FIG. 24.

FIGS. 22 and 23 show details of upper and lower round plate elements 204, 206. Elements 204, 206 include center holes 210 and 212, respectively, for receiving a bolt, pin, or other fastening means to couple to shaft 215 of servopositioner 214. The bottom of upper round plate element 204 includes a central area 205 that is slightly recessed to help achieve an optimal seal.

Flexible member 208 extends between upper housing 202 and mounting plate 218 and between upper and lower round plate elements 204, 206. As in the first embodiment described above, and as shown most clearly in FIG. 7, the portion of membrane 208 not sandwiched between these structural components, identified by reference numeral 208', has some gather (i.e. fold or wrinkle). The gather 208' permits plate elements 204, 206 to move vertically and ultimately create a pressure differential between upper and lower pressure chambers, as will be described. Member 208 is preferably circular, relatively thin, and manufactured from a rubber or other like flexible material.

Upper plate 220, shown in detail in FIGS. 24–27, is located below and fixed to mounting plate 218. Upper plate 220 includes a pair of O-ring seals 238, 240 that sit within grooves 242 at the bottom of upper plate 220. Seal 240 surrounds a pressure chamber 245 defined by upper plate 220 and th top of the holder of the capillaries, to be described. Seal 240 seals pressure chamber 245 (which remains at ambient pressure) from L-shaped passages 243a. Passages 243a provide a fluid connection between a cavity 251 (defined by the top of plate 220 and the bottom of plates 216, 218 and flexible member 208 see FIG. 7) and a another pressure chamber 247 (defined primarily by middle and lower plates 222 and 224see FIGS. 7 and 28–33). Seal 238 surrounds passages 243a and seals passages 243a from ambient environment. Upper plate 220 also includes an orifice 244 providing a fluid connection between the ambient environment and pressure chamber 245 (see FIG. 5) to maintain chamber 245 at ambient pressure. Upper plate 220 connects to points 219b of mounting plate 218 at mounting paints 219c.

Figure 5:
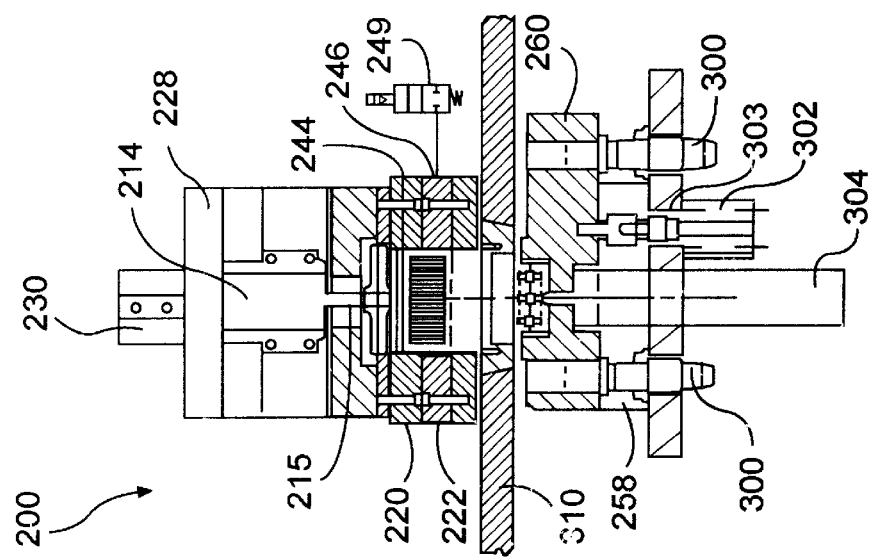
FIG. 5 is a cross-sectional side view of the device of FIG. 4.
Figure 28:
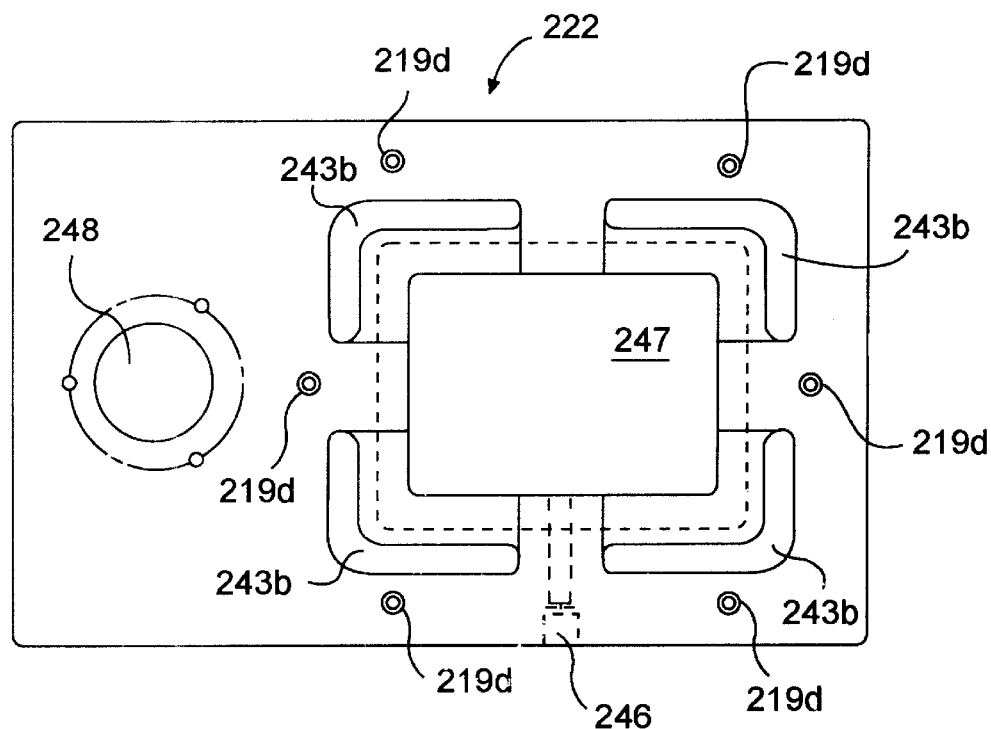
FIGS. 28–30 respectively are bottom, cross-sectional front, and top views of a middle plate of the print head of the device of FIG. 4, with FIG. 29 taken at line A—A of FIG. 30.
Figure 29:
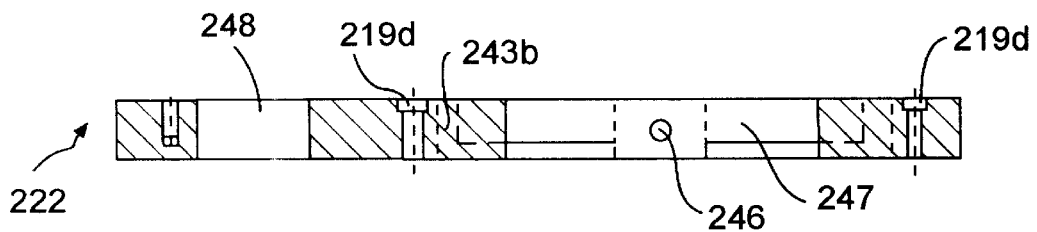
Figure 30:
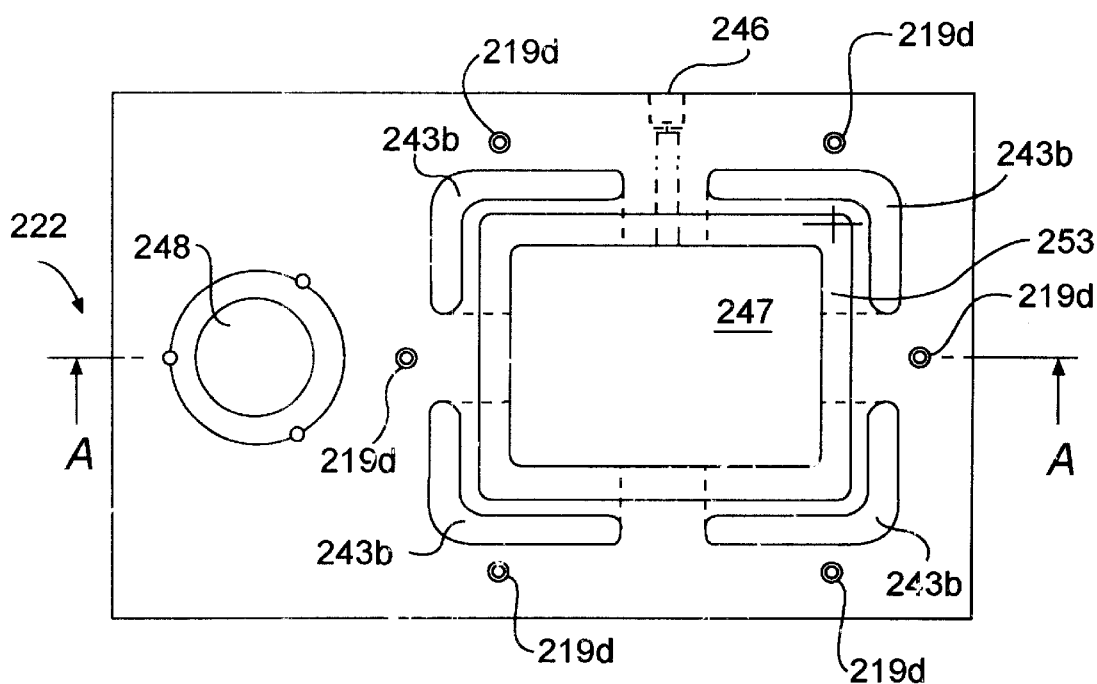
Figure 31:
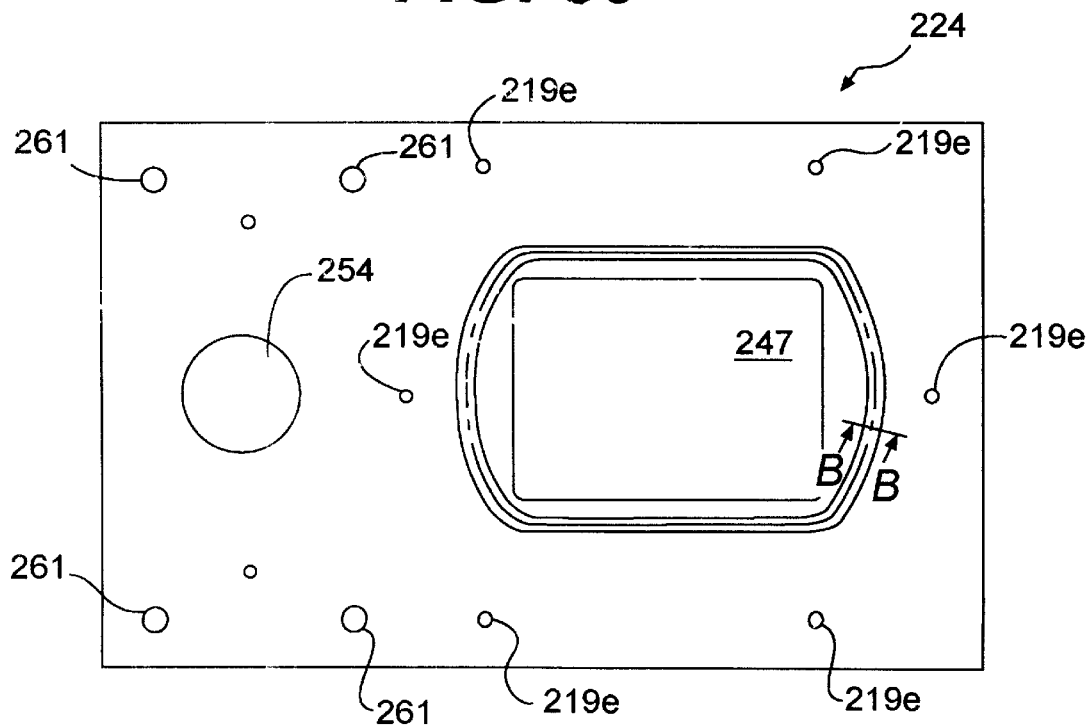
FIGS. 31–33 respectively are bottom, cross-sectional front, and top views of a lower plate of the print head of the device of FIG. 4, with FIG. 32 taken at line A—A of FIG. 33.
Figure 32:
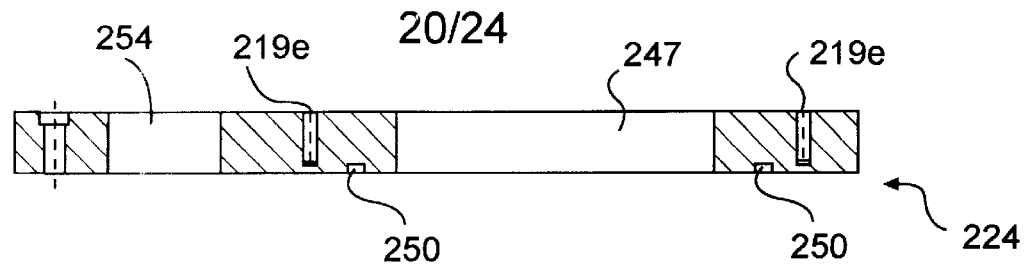
Figure 33:
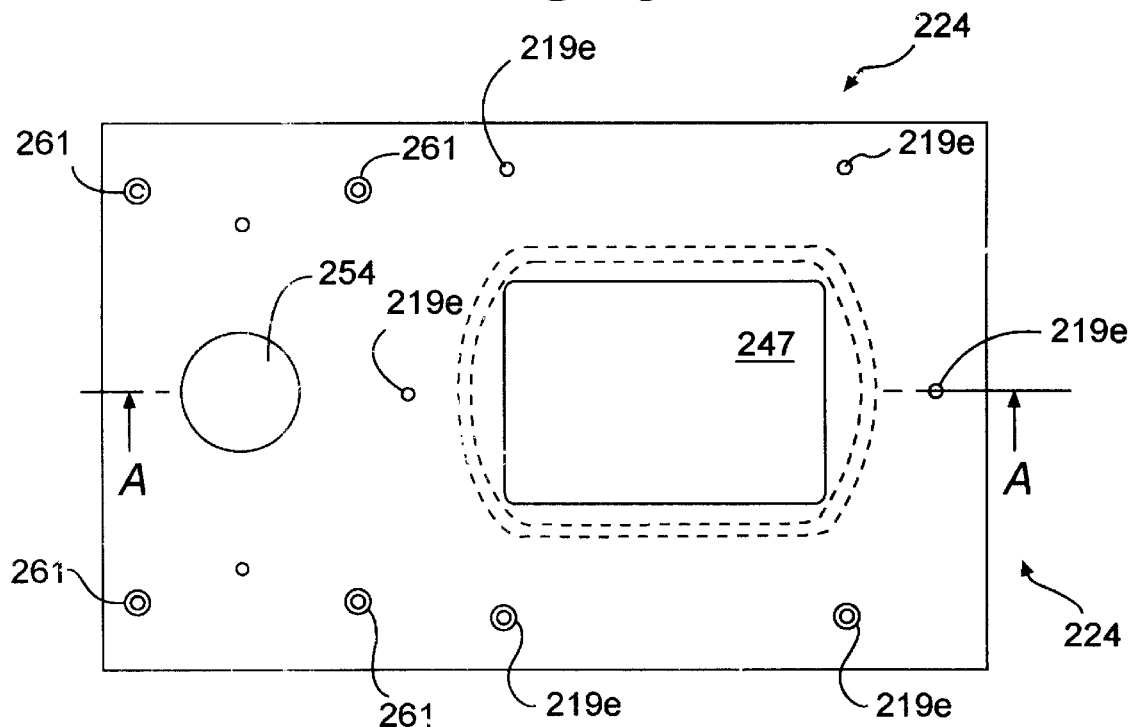
Figure 34:
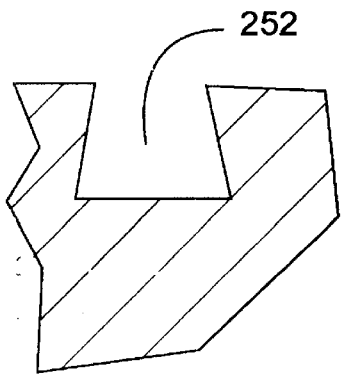
FIG. 34 is a partial cross-sectional view of the lower plate of FIGS. 31–33, showing a groove for an O-ring, taken at line B—B of FIG. 31.

Middle plate 222, shown in detail in FIGS. 28–30, is located below upper plate 220 and couples to points 219c of upper plate 220 at mounting points 219d. Middle plate 222 includes an orifice 246 in fluid connection with pressure chamber 247, Orifice 246 provides a fluid connection between a valve 249 and chamber 247, as shown in FIG. 5, to alter the pressure within chamber 247. More specifically, valve 248 raises the pressure within chamber 247 at the end of a print cycle by exposing chamber 247 to ambient condition and aerating chamber 247, as will be described. Middle plate 222 also includes L-shaped passages 243b that (along with passages 243a) provide a fluid connection between pressure chamber 247 and cavity 251. Middle plate 222 also includes a circular hole 248 for receiving linear ball bush guide 226.

A lower plate 224, shown in detail in FIGS. 31–34, is located beneath middle plate 220. Lower plate 224 includes an O-ring 250 seated within groove 252. O-ring 250 surrounds and seals chamber 247 from ambient surroundings. Lower plate 224 further includes a circular hole 254 to accommodate linear ball bush guide 226. Lower plate 224 mounts to points 219d of middle plate 222 at mounting points 219e.

Figure 6:
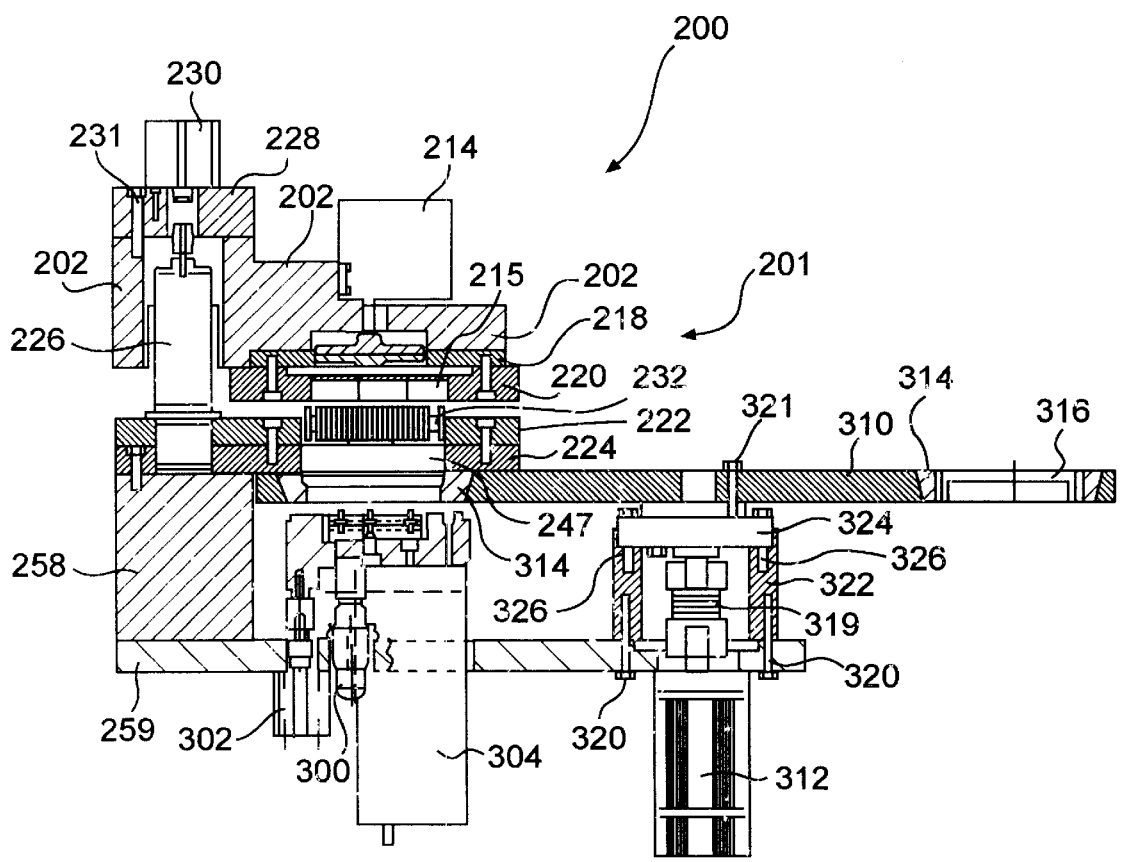
FIG. 6 is a cross-sectional front view of the device of FIG. 4 with a portion of its print head displaced vertically upwards.

As described, the connection between housing 202 and plates 218, 220, 222, and 224 occurs at mounting points 219a, b, c, d, e. As shown most clearly in FIG. 7, the preferable means of connecting these five components includes a pin or bolt 221 extending between each of points 219a, b, c, d, e. Each pin or bolt 221 is configured to permit upper plate 220 to separate from middle plate 222 for insertion and removal of a holder 232 of capillaries, as shown in FIG. 6. The scope of the present invention includes other means of connecting these components to achieve this purpose.

Figure 7:
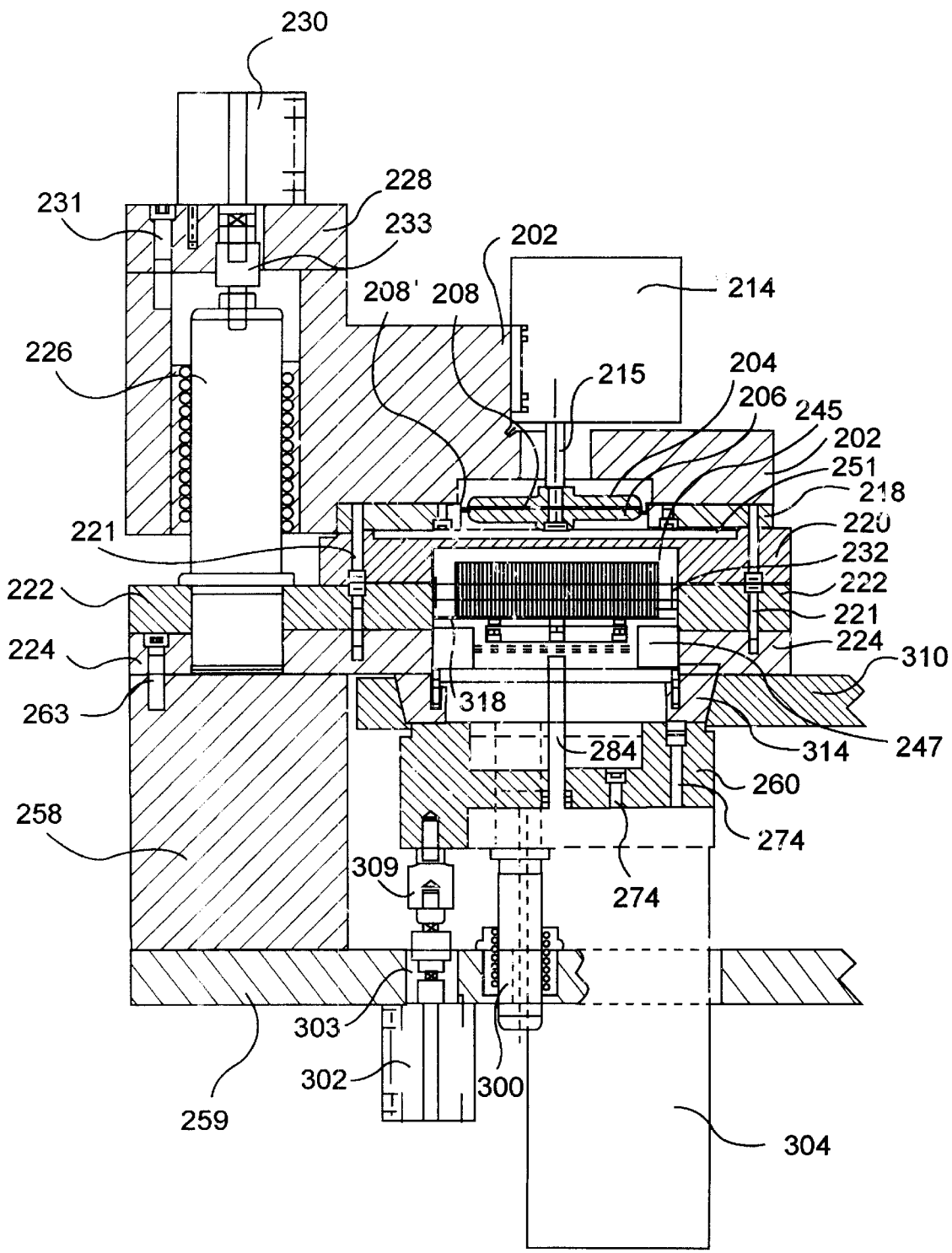
FIG. 7 is a partial cross-sectional front view of the device of FIG. 4 with a receiving plate positioned to receive liquid from capillaries.
Figure 8:
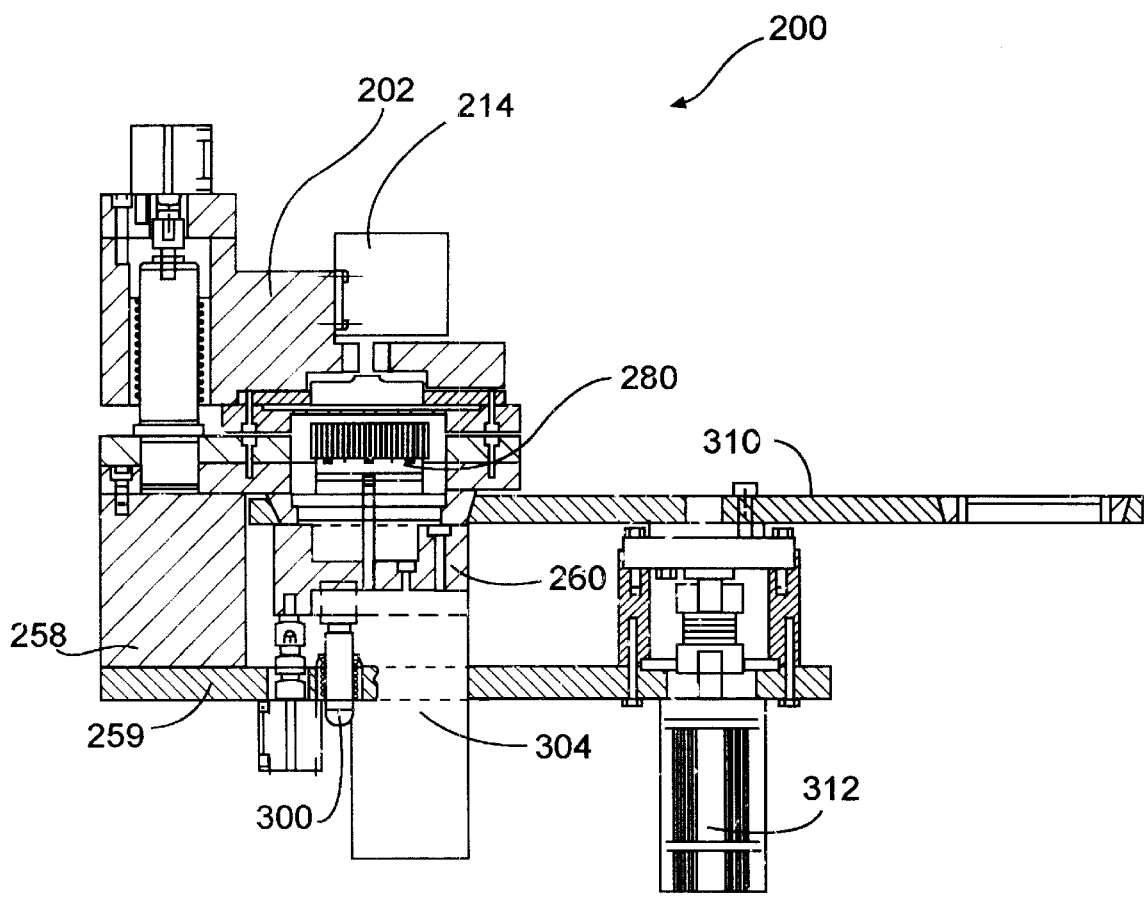
FIG. 8 is a cross-sectional front view of the device of FIG. 4 with a receiving plate positioned to receive liquid from capillaries.

As shown most clearly in FIGS. 6 and 7, mounting block 228 fixedly couples to an upper portion of upper housing 202 via mounting pins 231. As shown in FIG. 21, mounting pins 231 mount at points 229 of upper housing 202. Air cylinder 230 mounts above mounting block 228. Mounting block 228 includes a throughhole through which air cylinder 230 couples to linear ball bush guide 226. That coupling preferably includes a floating joint 233 and other suitable connection means, including, for example, bolts or pins. Air cylinder 230 controls the vertical movement of housing 202 and plates 218, 220 to separate plates 220 and 222 and permit insertion of a holder of capillaries, as will be described.

The bottom portion of dispensing device 200 includes the following main components: a mounting block 258; a bottom support plate 259; a pneumatically driven element 260; a gripper 280; a pair of ball bush guides 300; an air cylinder 302; a linear servodrive 304; and a servodrive 312. These components and their relationship and connection to each other will now be described in detail.

Mounting block 258 connects the top portion of dispensing device 200 to the bottom portion of device 200. Mounting block 258 connects to lower plate 224 at points 261 on plate 224 (see FIGS. 31–33) via bolts 263 (see FIG. 7) or other suitable fastening means. Mounting block 258 also connects to bottom support plate 259 which supports various components of the bottom portion of device 200.

Figure 35:
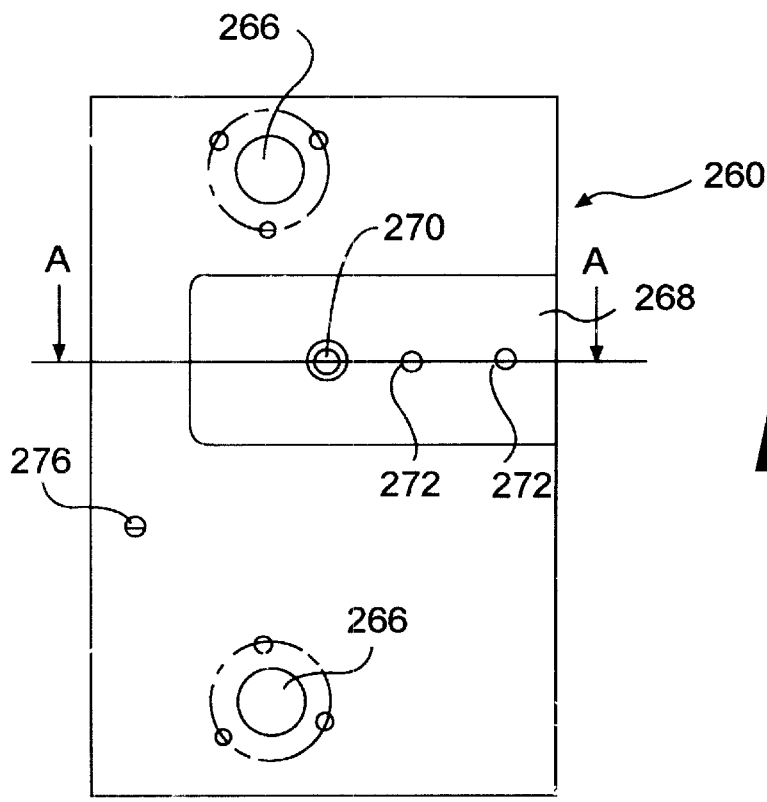
FIGS. 35–39 respectively are bottom, cross-sectional side, cross-sectional front, side, and top views of a pneumatically driven element of the device of FIG. 4, with FIG. 37 taken at lines A—A of FIGS. 35 and 39, and with FIG. 36 taken at line B—B of FIG. 37.
Figure 36:
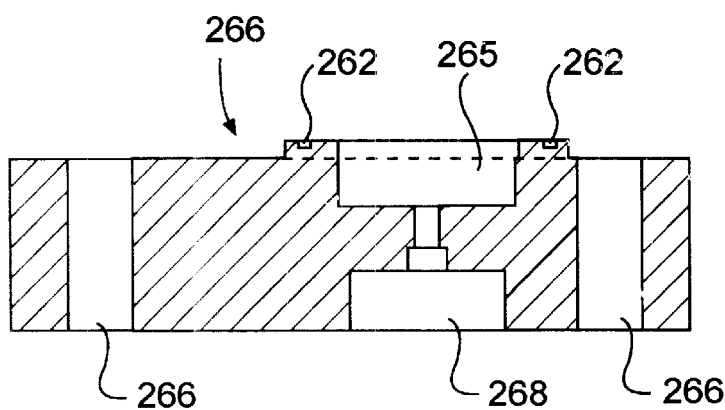
Figure 37:
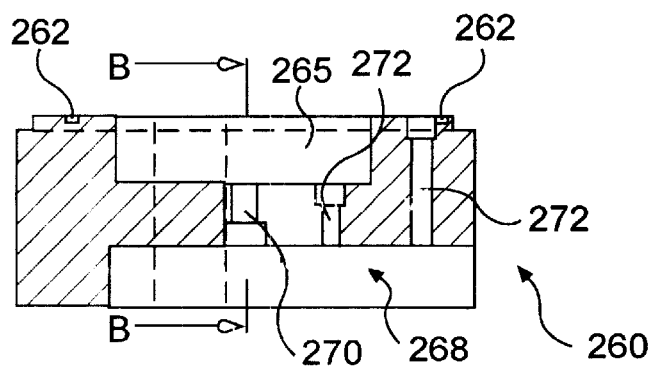
Figure 38:
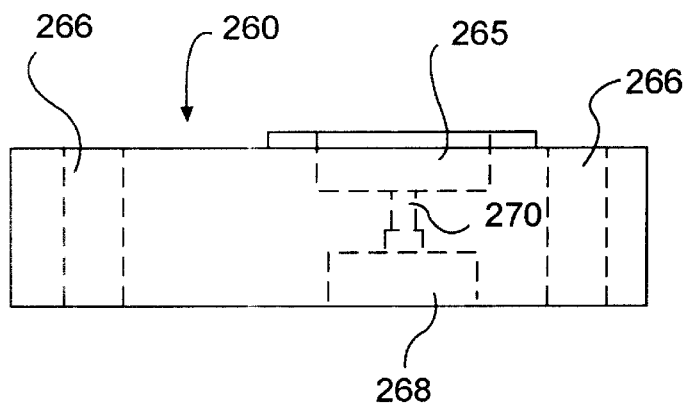
Figure 39:
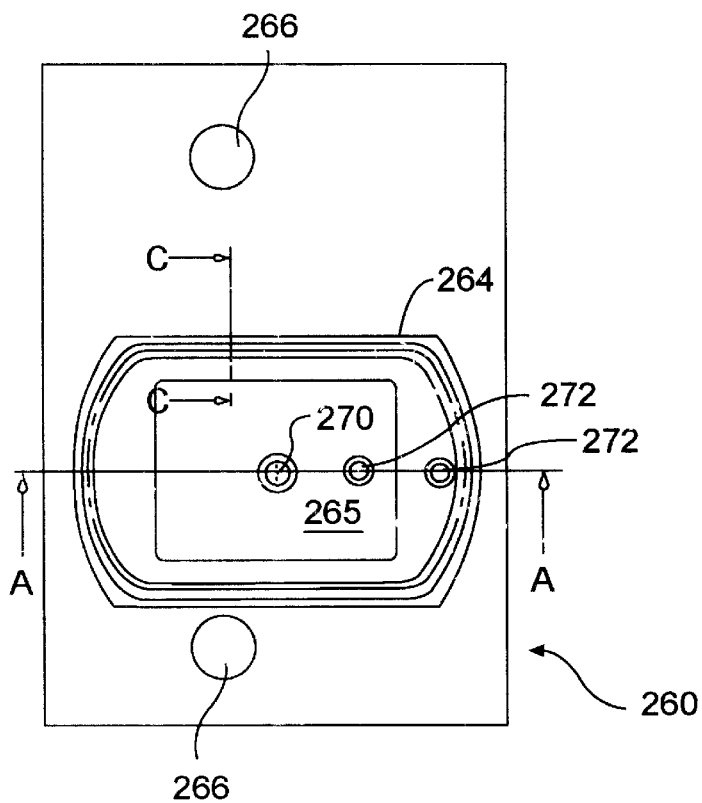
Figure 40:
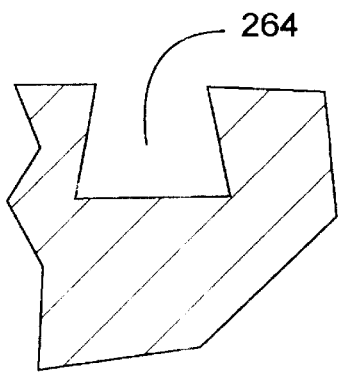
FIG. 40 is a partial cross-sectional view of the element of FIGS. 35–39, showing a groove for an O-ring, taken at line C—C of FIG. 39.

Pneumatically driven element 260 is shown in detail in FIGS. 35–40. FIG. 35 is a bottom view, whereas FIGS. 36–39 are cross-sectional side, cross-sectional front, side, and top views, respectively. The top of element 260 includes an O-ring 262 within a groove 264. O-ring 262 surrounds a cavity 265, also at the top of element 260. During operation, cavity 265 is in fluid connection with pressure chamber 247 and O-ring 262 sits between element 260 and a plate holder 314 (to be described). O-ring 262 seals cavity 265 (and thereby pressure chamber 247) from ambient surroundings. Element 260 also includes two circular throughholes 266 to accommodate linear ball bush guides 300. A bottom cavity 268 in element 260 accommodates linear servodrive 304. Servodrive 304 extends through a hole in plate 259 and couples to element 260 at mounting holes 272 via bolts 274 (see FIG. 7) or other suitable fastening means. Linear servodrive 304 also couples to a center mounting point 281 of gripper 280 by a shaft 284 (FIG. 7). Shaft 284 extends through a throughhole 270 in element 260. Linear servodrive 304 moves gripper 280 vertically. Suitable O-rings or other sealing structure may be included between shaft 254 and element 260 to seal cavity 265 (and thereby pressure chamber 247) from ambient surroundings during operation.

Figure 4:
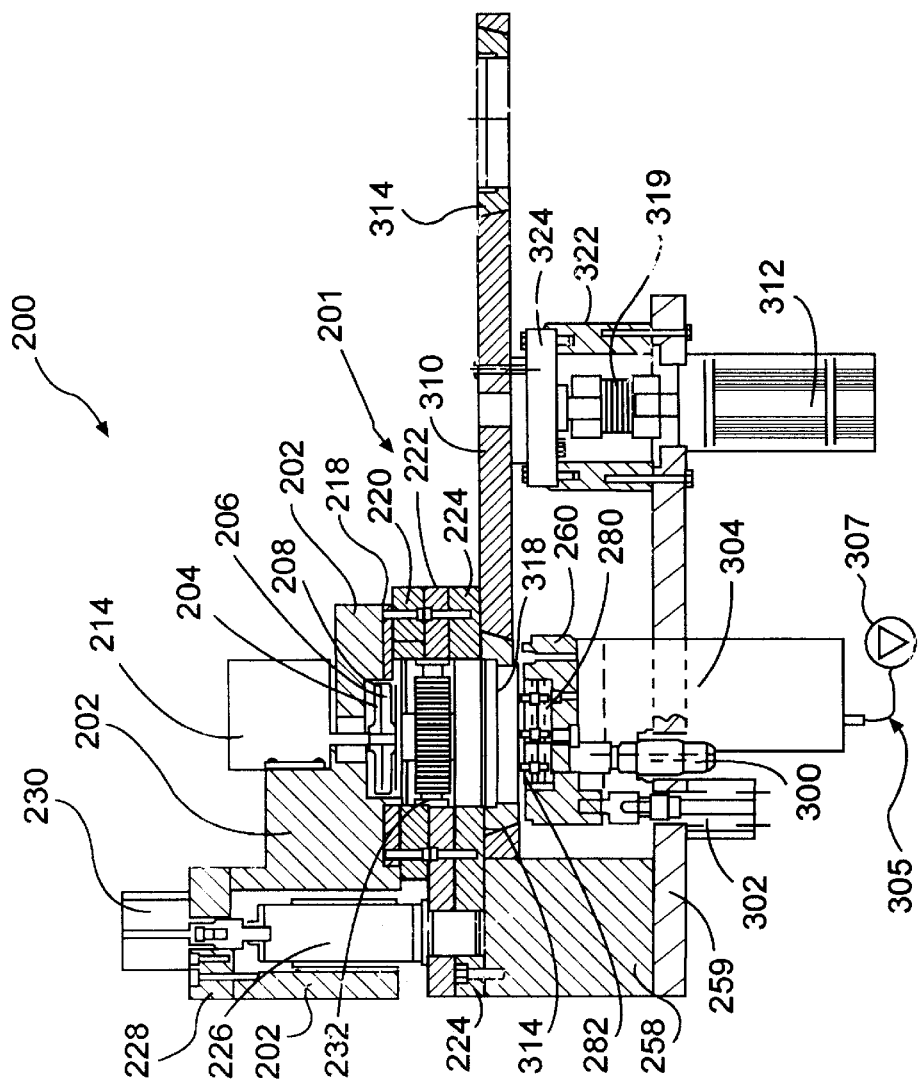
FIG. 4 is a cross-sectional front view of a dispensing device according to another embodiment of the present invention.
Figure 41:
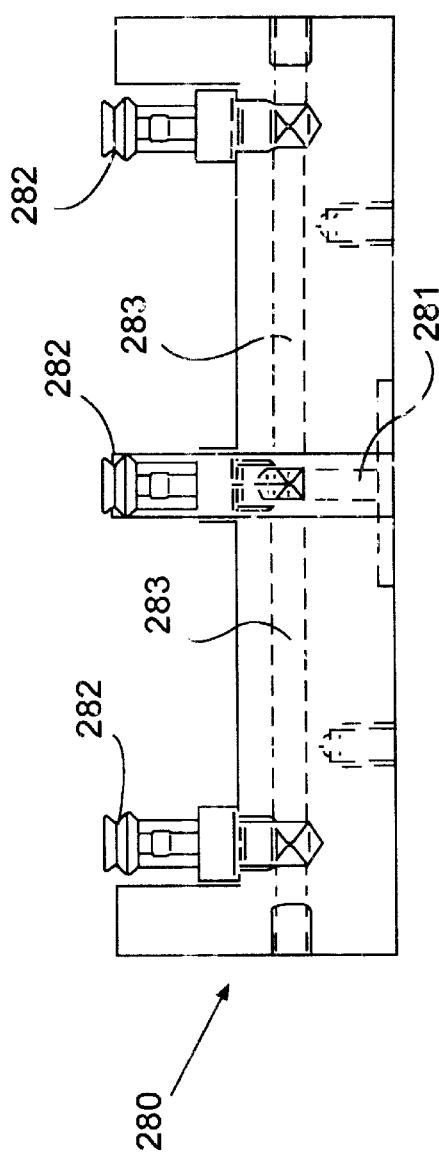
FIGS. 41–42 respectively are front and top views of a gripper of the device of FIG. 4.
Figure 42:
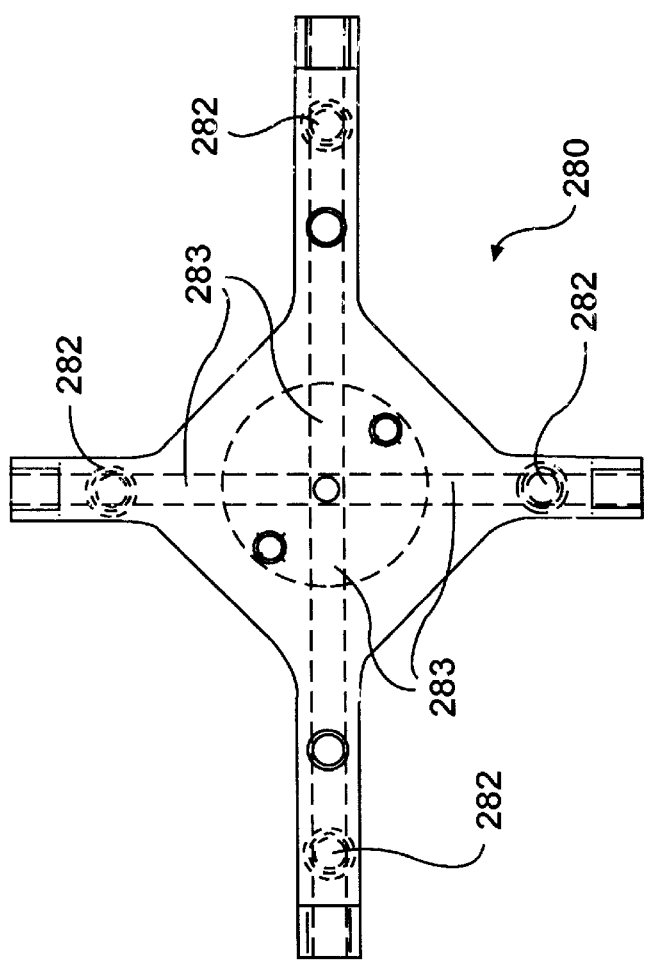

Gripper 280, shown in detail in FIGS. 41 and 42, mounts within cavity 265 of element 260. Gripper 280 includes a plurality of bellows 282 with suction cups at a top of bellows 282. FIGS. 41 and 42 show gripper 280 having four bellows 282 and corresponding suction cups at 90 degree intervals. It is to be understood that more or less bellows may be used as appropriate and still be within the scope of the present invention. Gripper 280 includes a manifold throughhole 283 for connecting the suction cups to a vacuum source. Shaft 284, connecting servodrive 304 to gripper 280, also includes a vacuum throughhole 283. The vacuum throughhole of shaft 284 also connects, via servodrive 304, to external vacuum tubing 305 extending from servodrive 304, as shown in FIG. 4. Vacuum tubing 305 connects to an external vacuum source 307, such as, for example, a pneumatically-driven, multi-stage ejector. External vacuum source 307 provides a vacuum through external tubing 305, servodrive 304, throughhole shaft 284, manifold throughhole 283, and to the suction cups. The vacuum at the suction cups permit gripper 280 to securely engage receiving plate 318 for accurate displacement of receiving plate 318.

Air cylinder 302 mounts to bottom plate 259. As best shown in FIG. 7, a shaft of air cylinder 302 extends through a throughhole 303 of plate 259 and mechanically couples to element 260. The coupling occurs via a floating joint 309 and a pin, bolt, or other like device extending to point 276 in element 260 (see FIG. 35). When actuated, air cylinder 302 raises or lowers element 260.

Two linear ball bush guides 300, best shown in FIG. 5, ensure vertical alignment when element 260 is moved vertically. Each guide 300 mounts to bottom plate 259, extends through plate 259, and is received within a hole 266 of pneumatically driven element 260.

Figure 9:
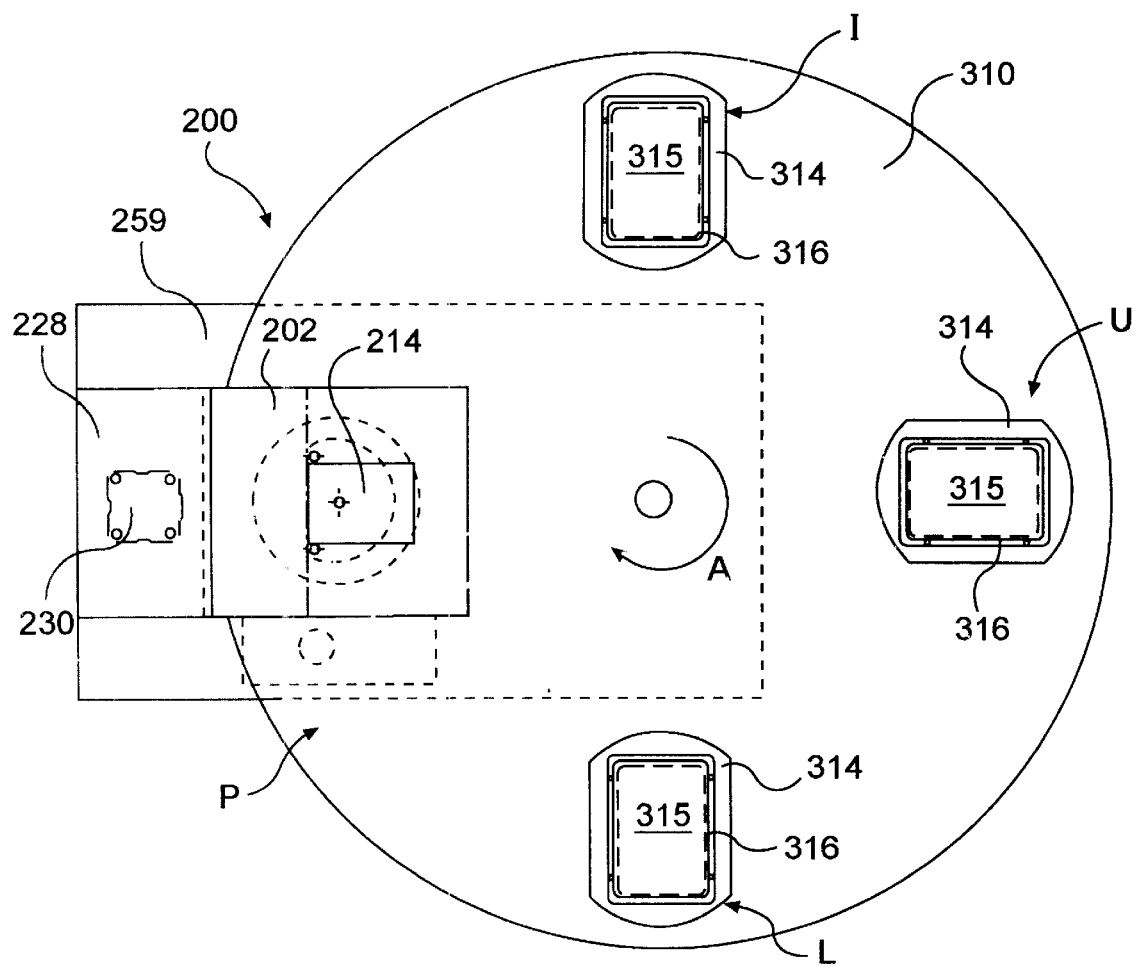
FIG. 9 is a top view of the device of FIG. 4.
Figure 10:
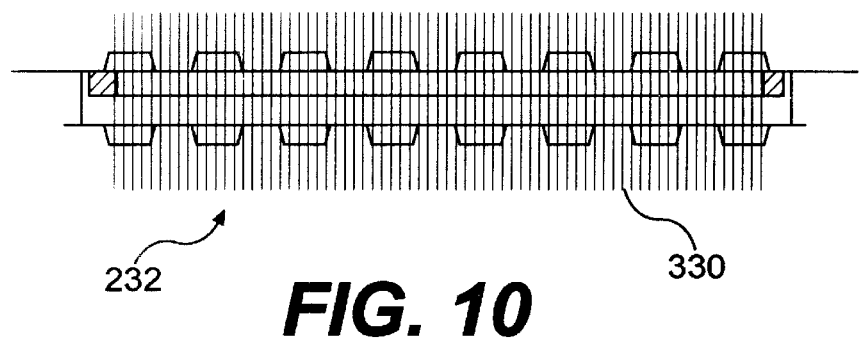
FIG. 10 is a front view of capillaries and a holder for use in a dispensing device according to embodiments of the present invention.
Figure 11:
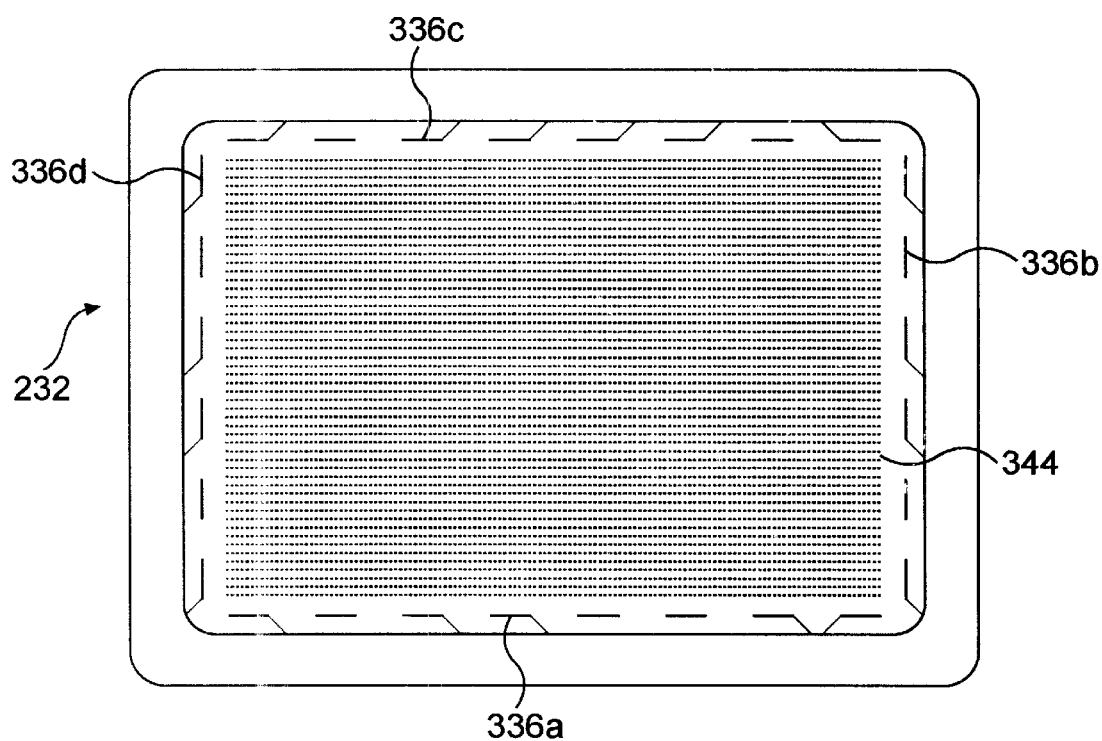
FIG. 11 is a top view of the capillaries and holder of FIG. 10.
Figure 12:
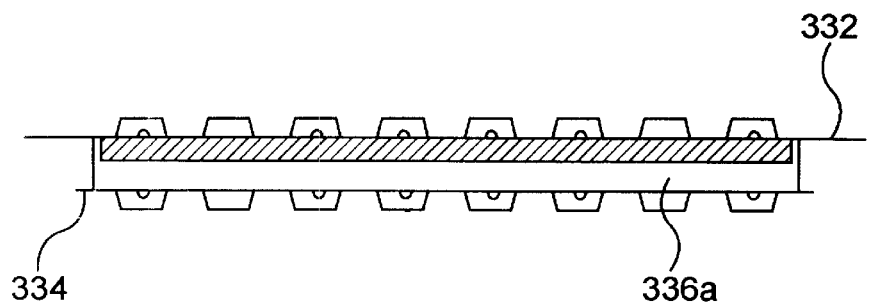
FIG. 12 is a front view of the holder of FIG. 10.
Figure 13:
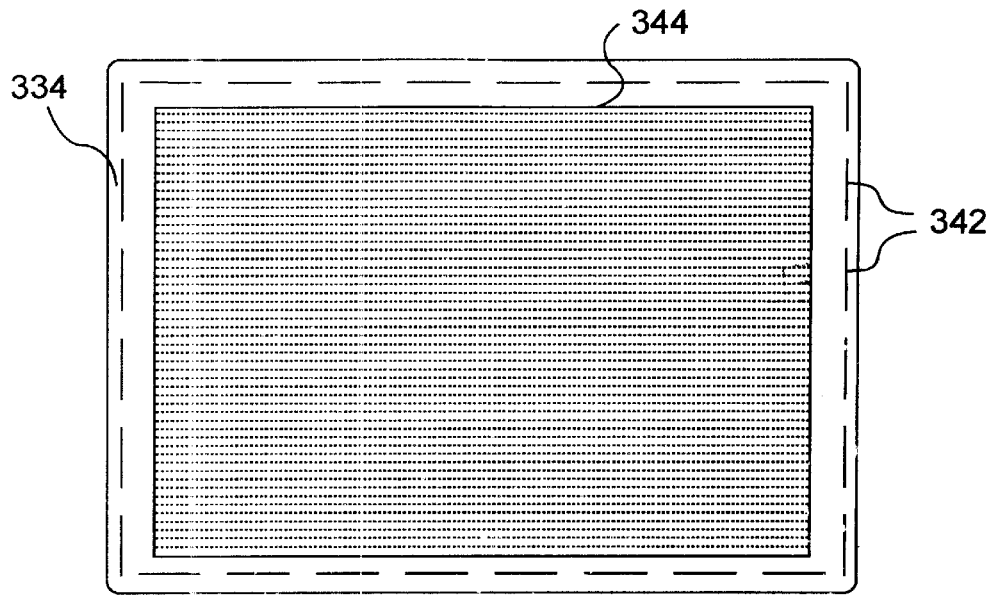
FIG. 13 is a top view of a bottom plate of the holder of FIG. 10.
Figure 14:
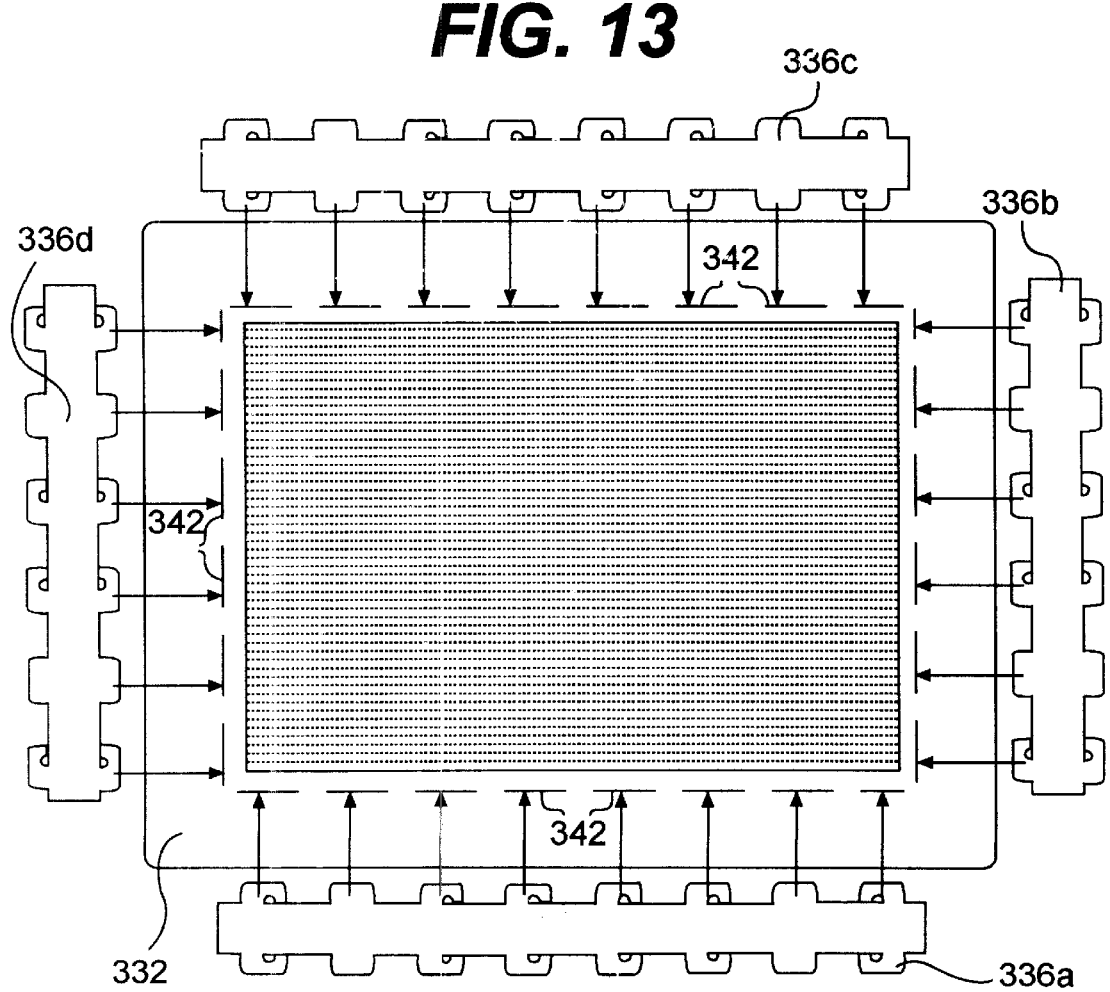
FIG. 14 is a bottom view of the top plate of the holder of FIG. 10 showing insertion of side plates.
Figure 15:
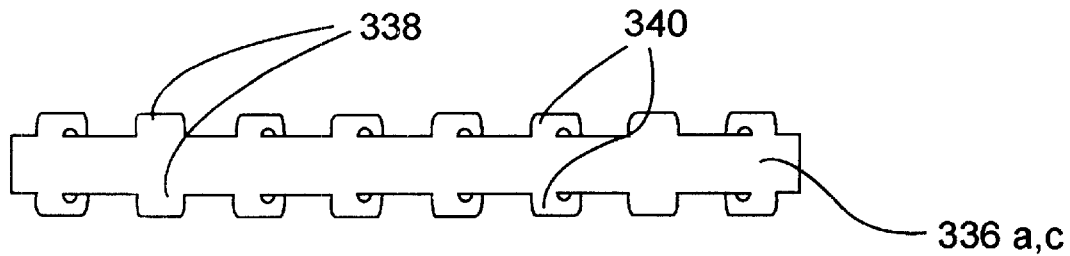
FIG. 15 is a front view of larger side plates of the holder of FIG. 10.
Figure 16:
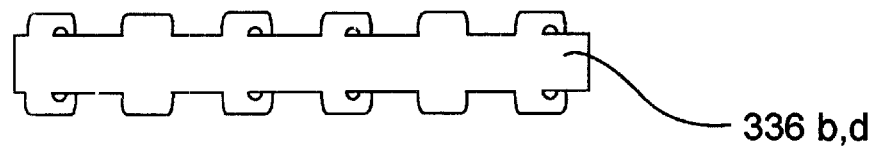
FIG. 16 is a front view of other smaller side plates for the holder of FIG. 10.

Turntable 310 mounts between the top and bottom portions of dispensing device 200. As shown most clearly in FIGS. 6 and 9, turntable 310 includes a plurality of throughholes each to receive a plate holder 314. Each plate holder 314 has a frustoconical shape corresponding to the shape of the throughhole in turntable 310. These corresponding shapes retain each plate holder 314 within turntable 310. FIG. 9 shows turntable 310 with four plate holders 314 arranged at 90 degree intervals around turntable 310. It is to be understood that any number of plate holders 314 preferably spaced at equal intervals within turntable 310 may be used and be within the scope of the present invention.

Each plate holder 314 includes a central cavity 315 and a seat 316 for supporting a receiving plate 318. Plate 318 lies loosely within holder 314. Receiving plate 318 may be a flat plate made of glass, plastic, or other suitable material, or may be a plate with a plurality of wells to receive liquid from the liquid dispensing members.

A servodrive 312 couples to turntable 310 to rotatably position turntable 310 and thereby accurately position a receiving plate 318 relative to a matrix of capillaries, to be described. As shown in FIG. 6, servodrive 312 extends through a throughhole in plate 259 and is coupled to a if bottom portion of a bellows coupling 319. The top portion of bellows coupling 319 is coupled to a bottom portion of a bearing 324. The top portion of bearing 324 is coupled to turntable 310 via a bolt 321 or other suitable like fastening means. Through these connections, servodrive 312 mechanically couples to turntable 310.

Bellows coupling 319 is contained within a housing 322. Housing 322 rigidly connects at its bottom to plate 259 via bolts 320 or other suitable like fastening means. Housing 322 rigidly connects at its top to bearing 324 via bolts 326 or other suitable like fastening means.

Figure 17A:
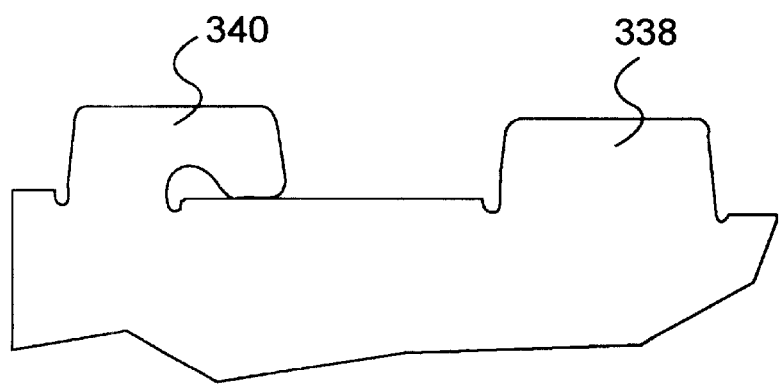
FIG. 17A is an enlarged partial front view of side plates for the holder of FIG. 10, showing two lip types.
Figure 17B:
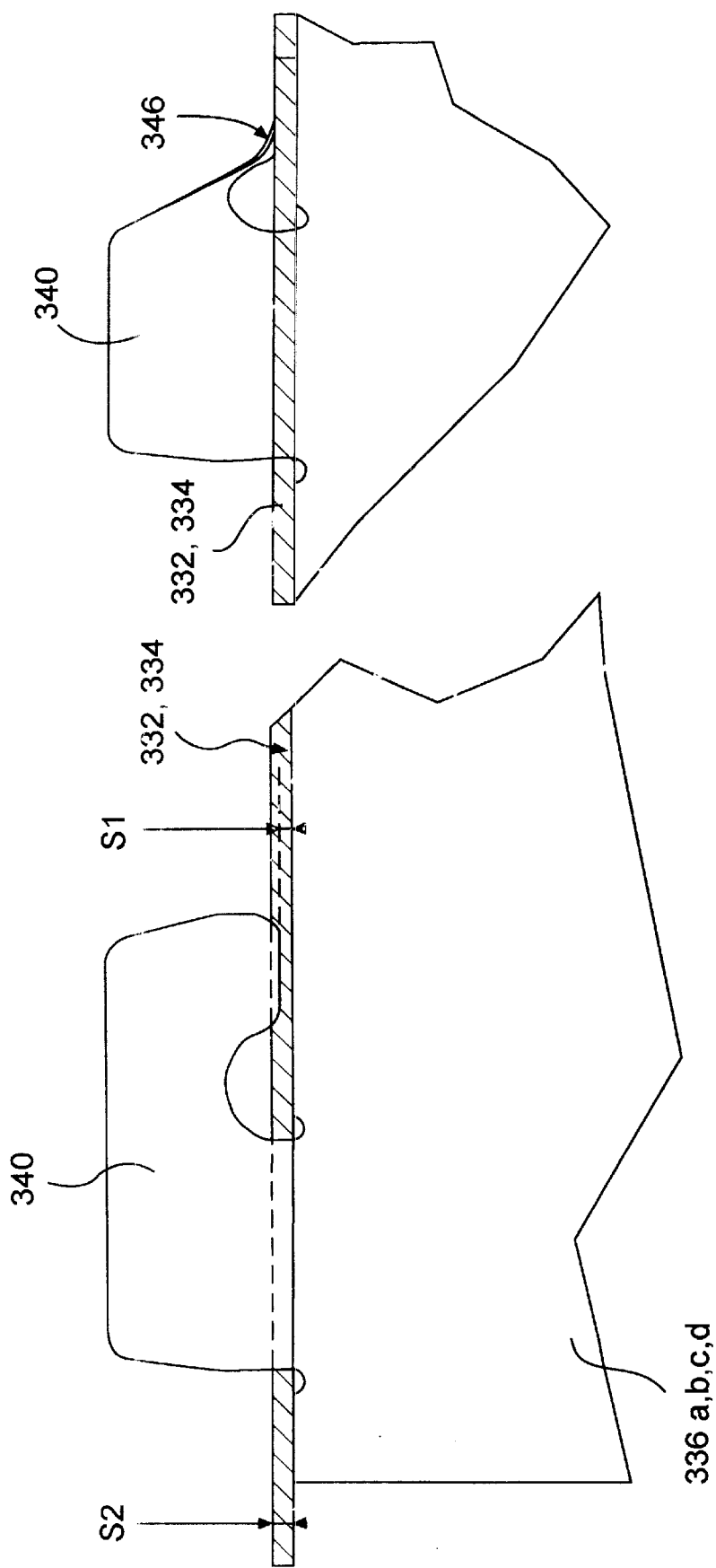
FIG. 17B is an enlarged front view of a lip type of a side plate, before and after the lip type is bent.

A holder 232 of liquid dispensing members, preferably capillaries 330, mounts within and separates pressure chambers 245, 247 of dispensing device 200. FIGS. 10–17 show details of holder 232. Holder 232 includes a top plate 332, a bottom plate 334, and side plates 336a,b,c,d to connect top and bottom plates 332, 334. Side plates 336 include lips 338 and 340 that slide within slots 342 of top and bottom plates 332, 334. Lips 338 are in the form of a flat planes and ensure alignment of top and bottom plates 332, 334. As shown in FIG. 17B, each lip 340 includes a hook that may be bent at, for example, a 45 degree angle, once lip 340 inserts within a slot 342. This creates tension to draw top and bottom plates 332, 334 towards side plates 336 and create a stable, rigid holder 232. More specifically, and with reference to FIG. 17B, top and bottom plates 332, 334 each have a thickness S2. Each hook of a lip type 340 is a distance S1 from a top edge of its side plate 336a, b, c, d. Distance S1 is less than thickness S2. Thus, when lip type 340 extends through a slot 342 of top or bottom plate 332, 334, the hook may be bent to engage a surface of top or bottom plate 332, 334, as shown by reference numeral 346 in FIG. 17B. This creates pressure on the surface of top or bottom plate 332, 334 at the bend, creating a rigid holder 232.

Top and bottom plates 332, 334 and side plates 336 are preferably made of copper and are preferably manufactured from a photochemical etching process to make wafer-thin sheets. Each of top and bottom plates 332, 334 includes a grid 344 of etched perforations. In an embodiment, grid 344 includes twelve rows of eight perforations to accommodate 96 capillaries 330. Grid 344, however, can have any number of rows of varying number of perforations to accommodate much higher numbers of capillaries. The grids 344 of plates 332 and 334 are accurately aligned to ensure alignment of capillaries 330 mounted therein. A thin coat of adhesive, preferably UV-sensitive glue, spread between capillaries 330 along top plate 332 fixes capillaries 330 in holder 232 and ensures that the bottom tips of capillaries 330 are in the same vertical position. The adhesive also acts to seal pressure chamber 245 above top plate 332 from pressure chamber 247 below top plate 332 when holder 232 is placed within dispensing device 200.

As shown in FIG. 6, holder 232 inserts within dispensing device 200 when top plate 220 is separated from middle plate 222. An outer rim of top plate 332 of holder 232 rests on a top surface of middle plate 222. More particularly, the outer rim of top plate 332 rests within a slightly recessed surface 253 of middle plate 222. The amount of recess of surface 253 is approximately the thickness of top plate 332 so that top plate 332 lies flush with the top surface of middle plate 222. When plates 220 and 222 close and sandwich the outer rim of top plate 332 therebetween, pressure chamber 245 is separated from pressure chamber 247. Chamber 245 is in fluid communication with the ambient environment via orifice 244, as shown in FIG. 5, and contains the open top of each capillary 330. Chamber 247 contains an open bottom of each capillary 330. Chambers 245 and 247 are sealed from one another by holder 232, and specifically top plate 332 and the sealing adhesive around capillaries 330. Whereas top plate 332 serves this sealing function, bottom plate 334 aids in aligning holder 232 and capillaries 330 therein.

Operation of dispensing device 200 will now be described in connection with FIGS. 4–9. Prior to operation of dispensing device 200, a liquid solution is aspirated into a plurality of capillaries 330, or other disposable dispensing members such as micropipettes. The aspirated liquid is retained inside capillaries 330 by capillary surface tension forces. Next, filled capillaries 330 are assembled into the etched perforations of holder 232 to form a high density grid of a plurality of filled capillaries 330. Capillaries 330 are assembled into any predetermined geometric distribution and preferably packed at a high density, for example twelve rows of eight capillaries. Capillaries 330 are then fixed into holder 232 by, for example, UV-sensitive glue, so that the bottom tip of each capillary 330 is at the same vertical position. The filling of the capillaries and assembly of capillaries into a holder may be done by any suitable method, including that described in PCT International Application No. PCT/IB 98/01399 entitled "Method for the Rapid Screening of Analytes" and filed Sep. 8, 1998, the entire disclosure of which is incorporated herein by reference.

Holder 232 with capillaries 330 then may be assembled into dispensing device 200. To do so, air cylinder 230 is actuated to move upwards and thereby lift housing 202 and a portion of print head 201, specifically plates 218 and 220. This causes top plate 220 to separate from middle plate 222. Upper housing 202 and its connected components, including plates 218, 220, servopositioner 214, round plates 204,206, are then swung clear to expose the upper surface of middle plates 222. These components swing about the axis of guide 226. An outer rim surface of top plate 332 of holder 232 then is set on plate 222. Housing 202 and its connected components then are swung back in place and air cylinder 230 is actuated to move downwards to lower housing 202 and rejoin plates 220 and 222. At this point, chamber 245 is hermetically sealed from chamber 247.

FIG. 9 shows four stations in turntable 310 of device 200. These stations are loading L, printing P, inspection and/or identification I, and unloading U. Turntable 310 rotates clockwise, as shown by arrow A in FIG. 9, to move a receiving plate 318 between stations. Plate 318 first, is loaded onto turntable 310 at loading station L. Printing onto receiving plate 318 occurs at printing station P. Receiving plate 318 may be inspected for quality and/or marked for identification purposes at station I. Receiving plate 318 then may be unloaded from turntable 310 at station U. All of these stations and their operations may be controlled by suitable computer software derived by one skilled in the art. As an alternative, a manual control panel may be provided at each station for control of the operations at each station. Moreover, robots or other peripherals may be provided at each station to perform the functions of that station. In addition, peripherals may be added between stations to perform appropriate additional functions. For example, a sensor may be provided between loading station L and printing station P to determine if a receiving plate 318 is located on turntable 310 prior to the printing operation.

Once receiving plate 318 has been loaded onto turntable 310 at station L, turntable 310 is rotated 90 degrees clockwise so that receiving plate 318 is positioned at printing station P. This situation is shown in FIGS. 4 and 5. Next, air cylinder 302 is actuated to displace element 260 upwards and force plate holder 314 upwards against bottom plate 224. The meshing of element 260, plate holder 314, and bottom plate 224 is shown in FIG. 7. FIG. 7 also shows the next step of the printing process, wherein servodrive 304 has been actuated to displace gripper 280 vertically so that its bellows 282 with suction cups engage receiving plate 318 and force receiving plate 318 vertically. Receiving plate 318 is moved vertically to a position just under the bottom tips of capillaries 330, as shown in FIG. 7. The optimal gap between the bottom tip of capillaries 330 and the top surface of plate 318 will depend on a variety of factors, as mentioned above.

The structural components of dispensing device 200 are now in position to begin a print cycle. The print cycle begins by actuating servodrive 214 to move plates 204 and 206 vertically downwards. It will be apparent that the movement of plates 204 and 206 downwards is optional, as a pressure differential between chambers 245 and 247 may be created without this movement. Next, pressure chamber 247 is plugged at orifice 246 by valve 249. While chamber 245 remains at ambient pressure due to orifice 244, a pressure drop is created in pressure chamber 247 by servodrive 214 displacing plates 204, 206 vertically upwards. The pressure drop is preferably sudden and brief and performed in a controlled manner similar to that described above in connection with FIGS. 1–3. Thus, a lower pressure will exist in pressure chamber 247 relative to pressure chamber 245. A top of each capillary 330 therefore will be exposed to a greater pressure than a bottom of each capillary 330 and a difference in pressure result across the liquid in each capillary 330. Similar to that described above in connection with FIGS. 1–3, a printed spot of liquid from each capillary 330 will form on receiving plate 318.

After the brief, sudden pressure drop, valve 249 is opened to expose pressure chamber 247 to ambient conditions and aerate chamber 247. This increases the pressure within pressure chamber 247 and equalizes the pressures within chambers 247 and 245. Servodrive 214 also may be actuated to return plates 204, 206 to their original position. As described earlier, capillary forces will dominate once again, forcing liquid to remain within each capillary 330.

At the same time, servodrive 304 is actuated to displace gripper 280 vertically downwards and reposition receiving plate 318 onto plate holder 314. Air cylinder 302 then is actuated to lower element 260 and thus lower plate holder 314 back into its original position within turntable 310. Next, turntable 310 is rotated clockwise so that receiving plate 318 enters inspection/identification station 1, where any number of suitable inspection, identification, or other post-printing functions may be performed. Receiving plate 318 then is rotated to unloading station U, where plate 318 may be unloaded.

This process may be repeated for any number of receiving plates 318 until liquid in the capillaries 330 has been used, resulting in a number of replica prints of the liquid within capillaries 330.

It will be apparent to those skilled in the art that various modifications and variations can be made to the dispensing device and related method of the present invention without departing from the scope or spirit of the invention. For example, the described embodiments employ a pressure drop in the chamber below the capillaries. Instead, the printing device may be configured so that a differential pressure generator creates a pressure rise in the chamber above the capillaries to result in a similar print cycle. In such a case, the upper chamber may be connected to the external environment to equalize the pressures in the chambers, as necessary.

As a further example, the present invention also encompasses moving the holder with capillaries toward a stationary receiving plate. Moreover, the described embodiments include various servodrives and air cylinders to perform many of the mechanical movements during printing. Any suitable actuation mechanisms may be used for these movements. In addition, any of various suitable elements for fastening the structural components of the dispensing device together may be used, and any suitable sealing element may be used in place of each described O-ring.

As an even further modification of the described device and method, the dispensing of liquid from the capillaries may be performed through controlled vibration of the liquid or the holder of the capillaries. In such a case, the differential pressure generator creates well-defined combinations of repeated pressure changes. These pressure changes, and the use of particular shaped capillaries, including a narrow open bottom end, can create standing waves in the liquid column inside the capillary. This can result in dispensing a stream of droplets.

The present invention covers all of these modifications and variations of this invention provided they come within the scope of the appended claims and their equivalents.

What is claimed is:

1. A device for dispensing liquid, comprising:
   a housing configured to contain a plurality of liquid dispensing members containing a liquid and configured to contain a receiving member in a receiving position to receive the liquid from the plurality of liquid dispensing members, the housing defining a first pressure chamber and a second pressure chamber, the first pressure chamber capable of being sealed relative to the second pressure chamber; and
   a differential pressure generator operably connected to one of the first and second pressure chambers, the generator capable of generating a pressure differential between the first and second pressure chambers to cause the plurality of liquid dispensing members to dispense liquid onto the receiving member.

2. The device of claim 1, wherein the first pressure chamber is in fluid communication with ambient environment.

3. A device for dispensing liquid; comprising:
   a housing configured to contain a plurality of liquid dispensing members containing a liquid and configured to contain a receiving member in a receiving position to receive the liquid from the plurality of liquid dispensing members, the housing defining a first pressure chamber and a second pressure chamber, the first pressure chamber capable of being sealed relative to the second pressure chamber; and
   a differential pressure generator operably connected to one of the first and second pressure chambers, the generator capable of generating a pressure differential between the first and second pressure chambers to cause the plurality of liquid dispensing members to dispense liquid onto the receiving member, further comprising a plug to selectively seal the second pressure chamber from the ambient environment.

4. The device of claim 3, wherein the plug includes a valve in fluid communication with the second pressure chamber.

5. The device of claim 1, wherein the housing is configured to hold a first end of each of the plurality of liquid dispensing members in the first pressure chamber and a second end of each of the plurality of liquid dispensing members and the receiving member in the second pressure chamber.

6. A device for dispensing liquid; comprising:
a housing configured to contain a plurality of liquid dispensing members containing a liquid and configured to contain a receiving member in a receiving position to receive the liquid from the plurality of liquid dispensing members, the housing defining a first pressure chamber and a second pressure chamber, the first pressure chamber capable of being sealed relative to the second pressure chamber; and
a differential pressure generator operably connected to one of the first and second pressure chambers, the generator capable of generating a pressure differential between the first and second pressure chambers to cause the plurality of liquid dispensing members to dispense liquid onto the receiving member, further comprising a plug to selectively seal the second pressure chamber from the ambient environment wherein the differential pressure generator is in communication with the second pressure chamber and is capable of creating a pressure in the second pressure chamber that is lower than a pressure in the first pressure chamber.

7. A device for dispensing liquid; comprising:
a housing configured to contain a plurality of liquid dispensing members containing a liquid and configured to contain a receiving member in a receiving position to receive the liquid from the plurality of liquid dispensing members, the housing defining a first pressure chamber and a second pressure chamber, the first pressure chamber capable of being sealed relative to the second pressure chamber; and
a differential pressure generator operably connected to one of the first and second pressure chambers, the generator capable of generating a pressure differential between the first and second pressure chambers to cause the plurality of liquid dispensing members to dispense liquid onto the receiving member, further comprising a plug to selectively seal, the second pressure chamber from the ambient environment wherein the differential pressure generator is in communication with a second pressure chamber and includes a movable member capable of altering a volume of the second pressure chamber to alter a pressure within the second pressure chamber.

8. The device of claim 7, wherein the movable member seals the second pressure chamber from ambient environment.

9. The device of claim 7, wherein the movable member includes a flexible member.

10. The device of claim 9, wherein the flexible member is between a pair of movable plates.

11. The device of claim 1, further comprising a support adjacent to the housing and capable of supporting a plurality of receiving members.

12. The device of claim 11, wherein the support is movable relative to the housing to position a receiving member in the housing.

13. The device of claim 11, wherein the support is moveable relative to the housing to sequentially position receiving members in the housing one receiving member at a time.

14. The device of claim 1, wherein the second pressure chamber is configured to contain the receiving member, and further comprising a positioning device within the second pressure chamber capable of positioning the receiving member in the receiving position.

15. The device of claim 14, wherein the positioning device includes a movable element having an end capable of gripping the receiving member.

16. A device for dispensing liquid, comprising:
a holder having a plurality of liquid dispensing members mounted therein, each of the plurality of liquid dispensing members configured to contain a liquid between first and second ends of the dispensing member;
a receiving member capable of receiving liquid dispensed from the plurality of liquid dispensing members;
a housing defining a first pressure chamber and a second pressure chamber, the first pressure chamber capable of being sealed relative to the second pressure chamber; and
a differential pressure generator operably connected to at least one of the first and second pressure chambers, the generator capable of generating a pressure differential between the first and second pressure chambers, wherein the housing is configured to contain the holder in a dispensing position and the receiving member in a receiving position so that the generation of the pressure differential causes the plurality of liquid dispensing members to dispense liquid onto the receiving member.

17. The device of claim 16, wherein the holder seals the first pressure chamber from the second pressure chamber.

18. The device of claim 16, wherein the first pressure chamber is in fluid communication with ambient environment and the second pressure chamber is capable of being selectively sealed from the ambient environment.

19. The device of claim 16, wherein each of the plurality of liquid dispensing members is a capillary.

20. The device of claim 19, wherein the housing is configured to contain the holder so that the first end of each capillary is in the first pressure chamber and the second end of each capillary is in the second pressure chamber.

21. The device of claim 20, wherein the differential pressure generator is in communication with the second pressure chamber and is capable of creating a pressure in the second pressure chamber that is lower than a pressure in the first pressure chamber.

22. A device for dispensing liquid, comprising:
a holder having a plurality of liquid dispensing members mounted therein, each of the plurality of liquid dispensing members configured to contain a liquid between first and second ends of the dispensing member;
a receiving member capable of receiving liquid dispensed from the plurality of liquid dispensing members;
a housing defining a first pressure chamber and a second pressure chamber, the first pressure chamber capable of being sealed relative to the second pressure chamber; and a differential pressure generator operably connected to at least one of the first and second pressure chambers, the generator capable of generating a pressure differential between the first and second pressure chambers, wherein the housing is configured to contain the holder in a dispensing position and the receiving member in a receiving position so that the generation of the pressure differential causes the plurality of liquid dispensing members to dispense liquid onto the receiving member, wherein the differential pressure generator includes a movable member capable of altering a volume of the second pressure chamber to create the pressure within the second pressure chamber.

23. The device of claim 22, wherein the movable member seals the second pressure chamber from ambient environment.

24. The device of claim 22, wherein the movable member includes a flexible member.

25. The device of claim 24, wherein the flexible member is between a pair of movable plates.

26. The device of claim 16, further comprising a support adjacent to the housing and capable of supporting a plurality of receiving members.

27. The device of claim 26, wherein the support is movable relative to the housing to sequentially position receiving members in the housing one receiving member at a time.

28. The device of claim 16, wherein the second pressure chamber is configured to contain the receiving member, and further comprising a positioning device within the second pressure chamber capable of positioning the receiving member in the receiving position.

29. The device of claim 28, wherein the positioning device includes a movable element having an end capable of gripping the receiving member.

30. A method of dispensing liquid from a plurality of liquid dispensing members onto a receiving plate, the method comprising the steps of:
positioning a plurality of liquid dispensing members into a dispensing device so that a first end of each dispensing member is contained in a first pressure chamber of the dispensing device and a second end of each dispensing member is contained in a second pressure chamber of the dispensing device;
positioning a receiving plate in the second chamber relative to the second ends of the dispensing members; and
creating a pressure differential between the first and second pressure chambers so that the dispensing members dispense liquid onto the receiving plate.

31. A method of dispensing liquid form a plurality of liquid dispensing members onto a receiving plate, the method comprising the steps of: positioning a plurality of liquid dispensing members into a dispensing device so that a first end of each dispensing member is contained in a first pressure chamber of the dispensing device and a second end of each dispensing member is contained in a second pressure chamber of the dispensing device;
positioning a receiving plate in the second chamber relative to the second ends of the dispensing members; and
creating a pressure differential between the first and second pressure chambers so that the dispensing members dispense liquid onto the receiving plate, wherein the creating step includes lowering a pressure in the second pressure chamber.

32. The method of claim 31, wherein lowering the pressure in the second pressure chamber includes increasing a volume of the second pressure chamber.

33. The method of claim 31, wherein the volume is increased by moving a movable member.

34. The method of claim 30, further comprising the step of sealing the first pressure chamber from the second pressure chamber.

35. The method of claim 34, wherein the sealing step includes positioning a holder of the plurality of liquid dispensing members between the first pressure chamber and the second pressure chamber.

36. The method of claim 30, wherein the first pressure chamber is exposed to an environment, and further comprising the step of sealing the second pressure chamber from the environment prior to the creating step.

37. A method of dispensing liquid form a plurality of liquid dispensing members onto a receiving plate, the method comprising the steps of:
positioning a plurality of liquid dispensing members into a dispensing device so that a first end of each dispensing member is contained in a first pressure chamber of the dispensing device and a second end of each dispensing member is contained in a second pressure chamber of the dispensing device;
positioning a receiving plate in the second chamber relative to the second ends of the dispensing members; and
creating a pressure differential between the first and second pressure chambers so that the dispensing members dispense liquid onto the receiving plate, further comprising, subsequent to the creating step, the step of equalizing pressures within the first and second pressure chambers.

38. The method of claim 37, further comprising the steps of:
removing the receiving plate from the second chamber; and
repeating the receiving plate positioning step, the pressure differential creating step, and the pressure equalizing step to dispense liquid onto a subsequent receiving plate.

39. The method of claim 30, wherein each of the plurality of dispensing members is a capillary, the first end is an open top end, and the second end is an open bottom end.

* * * * *

UNITED STATES PATENT AND TRADEMARK OFFICE
CERTIFICATE OF CORRECTION

PATENT NO. : 6,544,480 B1
DATED : April 8, 2003
INVENTOR(S) : Velghe et al.

It is certified that error appears in the above-identified patent and that said Letters Patent is hereby corrected as shown below:

Column 17,
Line 42, "seal, the" should read -- seal the --

Column 19,
Line 41, "liquid form" should read -- liquid from --

Column 20,
Line 21, "liquid form" should read -- liquid from --

Signed and Sealed this

Seventh Day of October, 2003

JAMES E. ROGAN
*Director of the United States Patent and Trademark Office*